(12) United States Patent
Nedergaard et al.

(10) Patent No.: US 9,616,075 B2
(45) Date of Patent: Apr. 11, 2017

(54) METHOD OF TREATING AND PREVENTING BRAIN IMPAIRMENT USING NA+-K+-2CL-COTRANSPORTER ISOFORM 1 INHIBITORS

(71) Applicants: Maiken Nedergaard, Webster, NY (US); Alexander Stanley Thrane, Oslo (NO); Vinita Rangroo Thrane, Oslo (NO)

(72) Inventors: Maiken Nedergaard, Webster, NY (US); Alexander Stanley Thrane, Oslo (NO); Vinita Rangroo Thrane, Oslo (NO)

(73) Assignee: University of Rochester, Rochester, NY (US)

( * ) Notice: Subject to any disclaimer, the term of this patent is extended or adjusted under 35 U.S.C. 154(b) by 79 days.

(21) Appl. No.: 14/415,968

(22) PCT Filed: Mar. 15, 2013

(86) PCT No.: PCT/US2013/032403
§ 371 (c)(1),
(2) Date: Jan. 20, 2015

(87) PCT Pub. No.: WO2014/014519
PCT Pub. Date: Jan. 23, 2014

(65) Prior Publication Data
US 2015/0202215 A1 Jul. 23, 2015

Related U.S. Application Data

(60) Provisional application No. 61/674,178, filed on Jul. 20, 2012.

(51) Int. Cl.
| | | |
|---|---|---|
| A61K 31/18 | (2006.01) |
| A61K 31/4152 | (2006.01) |
| A61K 31/454 | (2006.01) |
| A61K 31/635 | (2006.01) |
| A61K 31/192 | (2006.01) |
| A61K 31/44 | (2006.01) |
| A61K 31/196 | (2006.01) |
| A61K 31/4035 | (2006.01) |
| A61K 31/341 | (2006.01) |
| A61K 31/402 | (2006.01) |
| A61K 31/41 | (2006.01) |

(52) U.S. Cl.
CPC .......... *A61K 31/635* (2013.01); *A61K 31/18* (2013.01); *A61K 31/192* (2013.01); *A61K 31/196* (2013.01); *A61K 31/341* (2013.01); *A61K 31/402* (2013.01); *A61K 31/4035* (2013.01); *A61K 31/41* (2013.01); *A61K 31/4152* (2013.01); *A61K 31/44* (2013.01); *A61K 31/454* (2013.01)

(58) Field of Classification Search
None
See application file for complete search history.

(56) References Cited

U.S. PATENT DOCUMENTS

| | | |
|---|---|---|
| 8,008,283 B2 | 8/2011 | Hochman et al. |
| 2002/0082252 A1 | 6/2002 | Hochman |
| 2006/0035914 A1* | 2/2006 | Hochman .............. A61K 31/00 514/269 |
| 2006/0089350 A1 | 4/2006 | Hochman et al. |
| 2007/0149526 A1 | 6/2007 | Hochman et al. |
| 2011/0237554 A1 | 9/2011 | Jensen |
| 2012/0004225 A1 | 1/2012 | Wanaski et al. |
| 2012/0115919 A1 | 5/2012 | Mueller et al. |

FOREIGN PATENT DOCUMENTS

| | | |
|---|---|---|
| WO | 2006/110187 A2 | 10/2006 |
| WO | 2011/126733 A2 | 10/2011 |

OTHER PUBLICATIONS

Abu-Osba, et al., Pediatric Research, 20:1062 (1986).*
Jayakumar, et al., Journal of Hepatology, 54:272 (2011, but available online Sep. 7, 2010).*
Extended European Search Report for corresponding European Patent Application 13819969.0 (Mar. 22, 2016).
Jayakumar et al., "Na-K-Cl Cotransporter-1 in the Mechanism of Ammonia-Induced Astrocyte Swelling," J. Biol. Chem. 283(49):33874-82 (2008).
Kofuji et al., "Potassium Buffering in the Central Nervous System," Neuroscience 129:1045-1056 (2004).
Hertz et al., "Astrocyte-Neuron Interaction During One-Trial Aversive Learning in the Neonate Chick," Neuroscience and Biobehavioral Reviews 20(3):537-547 (1996).
Wang et al., "Blocking Early GABA Depolarization With Bumetanide Results in Permanent Alterations in Cortical Circuits and Sensorimotor Gating Deficits," Cereb. Cortex 21:574-587 (2011).

(Continued)

*Primary Examiner* — Michael Barker
(74) *Attorney, Agent, or Firm* — LeClairRyan, a Professional Corporation

(57) ABSTRACT

The disclosure relates to a method of treating and/or preventing brain impairment in a subject that has or is susceptible to ammonia neurotoxicity (increased plasma ammonia), by administering a Na-; —K+-2Cl- cotransporter isoform 1 ("NKCC1") inhibitor to the selected subject under conditions effective to treat and/or prevent brain impairment. The disclosure further relates to methods of maintaining the fundamental function of astrocytic potassium buffering and inhibiting accumulation of potassium star rounding astrocytes, both of which involve contacting astrocytes with a NKCC 1 inhibitor.

7 Claims, 20 Drawing Sheets

(56) References Cited

OTHER PUBLICATIONS

International Search Report and Written Opinion for corresponding International Application No. PCT/US2013/032403 (mailed Jun. 10, 2013).

* cited by examiner

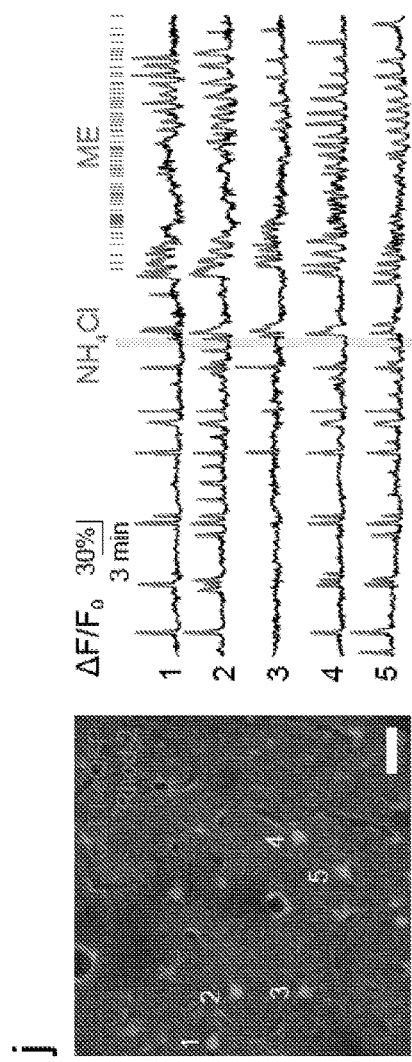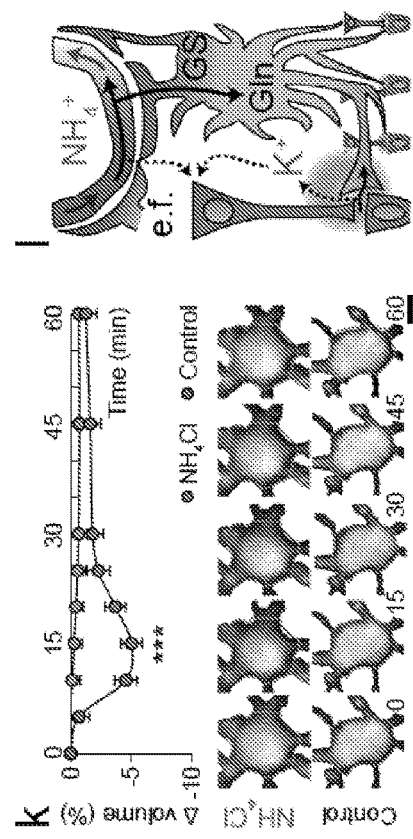
FIGURES 2J-2L

METHOD OF TREATING AND PREVENTING BRAIN IMPAIRMENT USING NA$^+$-K$^+$-2CL-COTRANSPORTER ISOFORM 1 INHIBITORS

This application is a national stage application under 35 U.S.C. 371 from PCT Application No. PCT/US2013/032403, filed Mar. 15, 2013, which claims the priority benefit of U.S. Provisional Patent Application Ser. No. 61/674,178, filed Jul. 20, 2012, which are hereby incorporated by reference in their entirety.

This invention was made with government support under grant numbers NS073390, NS056188, NS050315, NS038073, NS010350, and NS010337 awarded by the National Institutes of Health. The government has certain rights in this invention.

FIELD OF THE INVENTION

The present invention relates to methods of treating and preventing brain impairment using Na$^+$—K$^+$-2Cl$^-$ cotransporter isoform 1 ("NKCC1") inhibitors.

BACKGROUND OF THE INVENTION

Ammonia is a waste product of cellular metabolism that is constantly generated throughout the body. Ammonia exists as 99% NH$_4^+$ and 1% NH$_3$ at physiological pH, and is thus able to cross the blood-brain barrier by diffusing in its gas phase (NH$_3$). Cooper et al., "The Metabolic Fate of 13N-Labeled Ammonia in Rat Brain," *J. Biol. Chem.* 254:4982-4992 (1979). Ammonia homeostasis is vitally important in the brain, as an equimolar amount of ammonia is simultaneously released with glutamate during neuronal firing. Marcaggi et al., "Neuron-Glial Trafficking of NH$_4^+$ and K$^+$: Separate Routes of Uptake Into Glial Cells of Bee Retina," *Eur. J. Neurosci.* 19(4):966-976 (2004). If allowed to accumulate, ammonia causes brain dysfunction ranging from mild cognitive impairment, to seizures, coma, and death. Cagnon et al., "Hyperammonemia-Induced Toxicity for the Developing Central Nervous System," *Brain Res. Rev.* 56:183-197 (2007); Butterworth, R. F., "Pathophysiology of Hepatic Encephalopathy: A New Look at Ammonia," *Metab. Brain Dis.* 17:221-227 (2002). Ammonia is a ubiquitous waste product that accumulates in numerous metabolic disorders, causing neurological dysfunction ranging from learning impairment, to tremor, ataxia, seizures and coma. The brain is particularly vulnerable to ammonia as it readily crosses the blood-brain barrier and rapidly saturates its only removal pathway, glutamine synthetase, located in astrocytes. Nordström et al., "Effects of Phenobarbital in Cerebral Ischemia. Part I: Cerebral Energy Metabolism During Pronounced Incomplete Ischemia," *Stroke* 9(4):327-335 (1978).

Ammonia homeostasis is particularly important in the brain, as an equimolar amount of ammonia is simultaneously released with glutamate during neuronal firing. Marcaggi et al., "Neuron-Glial Trafficking of NH4$^+$ and K$^+$: Separate Routes of Uptake Into Glial Cells of Bee Retina," *Eur. J. Neurosci.* 19(4):966-976 (2004). Brain ammonia is almost exclusively detoxified by condensation with glutamate to form glutamine, a reaction catalyzed by glutamine synthetase with a rapid half-life of less than 3 seconds. Cooper, A. J., "13N as a Tracer for Studying Glutamate Metabolism," *Neurochemistry International* 59:456-464 (2011). Interestingly, glutamine synthetase has a higher affinity for ammonia than glutamate, suggesting that the removal of ammonia is prioritized over an excitotoxic neurotransmitter. Waniewski, R. A., "Physiological Levels of Ammonia Regulate Glutamine Synthesis From Extracellular Glutamate in Astrocyte Cultures," *J. Neurochem.* 58:167-174 (1992).

The current literature points to astrocytes as the primary target of ammonia toxicity, as they are the only cell type in the brain that express glutamine synthetase. Martinez-Hernandez et al., "Glutamine Synthetase: Glial Localization in Brain," *Science* 195(4284):1356-1358 (1977). Astrocytes have been shown to swell when exposed to ammonia in histological and cell culture studies. Butterworth, R. F., "Pathophysiology of Hepatic Encephalopathy: A New Look at Ammonia," *Metab. Brain Dis.* 17:221-227 (2002); Jayakumar et al., "Na—K—Cl Cotransporter-1 in the Mechanism of Ammonia-Induced Astrocyte Swelling," *J. Biol. Chem.* 283:33874-33882 (2008). However, there has been little progress in developing successful therapies, as the causal mechanism of ammonia toxicity remains unclear. Does astrocyte swelling contribute to the initial deterioration of neurological functions characteristic of acute ammonia toxicity, or is there a failure of other astrocytic homeostatic functions?

The present invention is directed to overcoming these and other deficiencies in the literature by targeting a novel disease mechanism that may be more important to symptom development in ammonia neuro-toxicity.

SUMMARY OF THE INVENTION

A first aspect of the present invention relates to a method of treating or preventing brain impairment in a subject. The method includes selecting a subject having or susceptible of having ammonia neurotoxicity and administering a Na$^+$—K$^+$-2Cl$^-$ cotransporter isoform 1 ("NKCC1") inhibitor to the selected subject under conditions effective to treat or prevent brain impairment.

A second aspect of the present invention relates to a method of inhibiting accumulation of potassium surrounding astrocytes. The method includes contacting astrocytes with a NKCC1 inhibitor under conditions effective to inhibit accumulation of potassium surrounding the astrocytes.

A third aspect of the present invention relates to a method of maintaining astrocytic potassium buffering. The method includes contacting astrocytes with a NKCC1 inhibitor under conditions effective to maintain astrocytic potassium buffering.

The present invention shows that neurotoxicity is not mediated by astrocyte swelling in vivo, as is widely believed and stated in the literature. Instead, the data indicates that ammonia rapidly compromises astrocyte potassium buffering, leading to an increase in extracellular potassium. This consequent increase in extracellular potassium overactivates NKCC1 activity and depolarizes the neuronal GABA reversal potential, thus impairing cortical inhibitory networks Inhibiting NKCC1 with the clinically used diuretic, bumetanide, potently treats the ammonia-induced neurological dysfunction. This data identifies failure of potassium buffering in astrocytes as a central mechanism in ammonia neurotoxicity, and suggests that bumetanide constitutes a novel therapeutic option for disorders of ammonia handling. The present invention finds that ammonia exerts its neurotoxic effects by compromising astrocyte potassium buffering, forcing an over activation of Na$^+$—K$^+$-2Cl$^-$ cotransporter that leads to an impairment of inhibitory (GABAergic) neurotransmission.

In order to elucidate the mechanisms responsible for ammonia toxicity in the brain, the present invention utilized an Otc$^{spf\text{-}ash}$ mouse model. These mice had an X-linked mutation in the gene encoding ornithine transcarbamylase (Otc), a urea cycle enzyme essential for liver detoxification of ammonia. Otc$^{spf\text{-}ash}$ mice are prone to developing rapid rises in plasma ammonia leading to severe neurological dysfunction, seizures, and coma. Ye et al. "Adenovirus-Mediated In Vivo Gene Transfer Rapidly Protects Ornithine Transcarbamylase-Deficient Mice From an Ammonium Challenge," *Pediatr. Res.* 41:527-535 (1997), which is hereby incorporated by reference in its entirety. Importantly, clinically relevant ammonia neurotoxicity can be studied in the absence of hepatic complications using the Otc$^{spf\text{-}ash}$ mice, without the additional liver complications associated with other frequently used models, such as acute liver failure. Ammonia neurotoxicity in the context of acute liver failure, on the other hand, is associated with numerous ammonia-independent changes (e.g., neuroinflammation) that compound the neurological phenotype. Thrane et al., "Real-Time Analysis of Microglial Activation and Motility in Hepatic and Hyperammonemic Encephalopathy," *Neuroscience* 220:247-55 (2012), which is hereby incorporated by reference in its entirety. Otc$^{spf\text{-}ash}$ mice thus provide an optimal model to study the direct effects of ammonia on the brain. Interestingly, elevated ammonia levels also predispose to seizures in children with normal urea cycle function, and can be caused by multiple factors including antiepileptic drugs themselves. Yamamoto et al., "Risk Factors for Hyperammonemia in Pediatric Patients With Epilepsy," *Epilepsia* (Epub Feb. 14, 2013), which is hereby incorporated by reference in its entirety.

In this study, in vivo optical imaging and electrophysiology were used in awake behaving Otc$^{spf\text{-}ash}$ mice, which allowed a detailed characterization and assessment of the early mechanisms involved in ammonia toxicity. It was found that earlier stages of ammonia neurotoxicity are characterized by a failure of astrocyte potassium buffering, rather than astrocyte swelling. The consequent increase in extracellular potassium ($[K^+]_o$) drives a NKCC1-dependent depolarizing shift in the neuronal γ-aminobutyric acid (GABA) reversal potential ($E_{GABA}$). The depolarized $E_{GABA}$ in ammonia neurotoxicity thus leads to a rapid impairment of neuronal inhibition. Bumetanide is a specific inhibitor of NKCC1 that is routinely used in clinical practice to treat fluid retention, with a favorable side effect profile. Hannaert et al., "Rat NKCC2/NKCC1 Cotransporter Selectivity for Loop Diuretic Drugs," *Naunyn Schmiedebergs Arch. Pharmacol.* 365:193-199 (2002), which is hereby incorporated by reference in its entirety. In the awake mouse model of the present invention, it was found that conditional deletion of NKCC1 or selective inhibition with bumetanide restored inhibitory transmission and protected the mice from ammonia-related neurological dysfunction.

BRIEF DESCRIPTION OF THE DRAWINGS

FIG. 1A shows that Otc$^{spf\text{-}ash}$ mice deficient in the liver enzyme ornithine transcarbamylase (Otc) are unable to metabolize ammonia to urea and excrete it via the kidney. Excess ammonia accumulates in the brain, where it is metabolized by astrocytic glutamine synthetase (GS) through amination of glutamate (Glu) to glutamine (Gln). Ammonia neurotoxicity progresses through stages characterized by stereotypical neurological features (e.g., ataxia). FIG. 1B, in the left panel, shows a diagram of automated video movement analysis. The right panel of FIG. 1B shows decreased spontaneous mouse movement in ammonia neurotoxicity. *P<0.001, n=8 (NH$_4$Cl) and 5 (Ctrl), Mann-Whitney U test. FIG. 1C, in the left panel, shows diagrams of sensory-motor phenotype scoring. The right panel shows that phenotype score increases sensitively after the ammonia load (7.5 mmol kg$^{-1}$) in Otc$^{spf\text{-}ash}$ mice, followed by a slow recovery. *P<0.001, n=8 (NH$_4$Cl) and 5 (Ctrl), Mann-Whitney U test. FIG. 1D shows baseline deficit in spatial learning in Otc$^{spf\text{-}ash}$ mice shown using fear chamber conditioning. *P=0.014, n=5 for each group, Mann-Whitney U test. FIG. 1E shows representative recordings of tonic-clonic seizures and myoclonic events during hyperammonemia. In FIG. 1F, myoclonic polyspike and wave discharges on EEG precede EMG responses. n=10. FIG. 1G shows that seizure and behavioral phenotypes worsen with increasing doses of ammonia, but are suppressed by anesthesia (pooled data for ketamine, isoflurane, urethane). *1$^3$<0.01, n=6 for each group, Kruskall-Wallis test. In FIG. 1H, 10 consecutive sweeps of field excitatory post-synaptic potentials (fEPSP) elicited by paired-pulse whisker stimulation before, during, and after cortical NH$_4$Cl application (10 mM, red box). In FIG. 1I, the paired-pulse ratio (PPR) increases during ammonia superfusion, indicating an impairment of cortical inhibitory networks. *P<0.001, n=10, paired t test. Data are shown as mean±SEM.

FIGS. 2A-2L show that ammonia compromises astrocyte potassium buffering by competing with potassium for uptake. In FIG. 2A (left panel), double-barreled ISM were used to record $[NH_4^+]_o$, $[K^+]_o$ and electroencephalogram (EEG) from layer II cortex of awake mice. Two-photon imaging was used to record astrocyte calcium signaling and volume changes. The right panel shows the calibration curves for NH$_4^+$ and K$^+$ ISMs. FIG. 2B shows representative NH$_4^+$ (top panel) and K$^+$ (bottom panel) ISM traces following i.p. injection (red box) of either ammonia (NH$_4$Cl) or saline (Ctrl). Vertical red lines indicate individual ME. FIG. 2C is a representative ISM trace (top panel) and scatterplot (bottom panel) showing an increase in $[K^+]_o$ prior to seizure onset with cortical application of ammonia (red box). Red lines indicate individual myoclonic events and red arrow indicates their mean onset. *P<0.001, n=10 (ammonia) and 7 (control), Mann-Whitney U test. FIG. 2D depicts the linear regression of seizure frequency and $[K]_o$ during ammonia neurotoxicity. n=8 (NH$_4$Cl i.p.) and 10 (cortical NH$_4$Cl application, Ctx). FIG. 2E, in the top panel, shows representative K$^+$ ISM trace during direct potassium application to the cortex. The bottom panel shows that KCl application causes multiple myoclonic events (red lines). FIGS. 2F and 2G show 10 consecutive sweeps of fEPSP elicited by paired-pulse whisker stimulation before, during, and after cortical KCl application (12.5 mM, red box). *P=0.028, n=6, Wilcox on signed ranks test. FIG. 2H illustrates Na$^+$—K$^+$-ATPase-dependent (ouabain-sensitive) uptake of potassium analogue rubidium ($^{86}$Rb$^+$) in cultured astrocytes, normalized to vehicle. *P<0.0001, n=23 (0 mM), 17 (0.5 mM), 16 (2 mM), 10 (5 mM), 10 (10 mM), one-way analysis of variance (ANOVA). FIG. 2I shows that NH$_4$Cl (15 mM) can substitute KCl (15 mM) as a substrate for the Na$^+$—K$^+$-ATPase in a cell-free assay of astrocyte cultures. n.s.=not significant, P=0.49, n=4 for each group, Mann-Whitney U test. FIG. 2J (left panel), depicts a representative image showing eGFP expressing astrocytes loaded with calcium indicator rhod-2 imaged 100 µm below the pial surface using 2PLSM. Scale bar represents 30 µm. The right panel shows corresponding rhod-2 intensity traces showing increased and desynchronized calcium transients following an ammonia load (7.5 mmol kg$^{-1}$) in an awake Otc$^{spf-ash}$ mouse. FIG. 2K shows that 3D real-time volume analysis using xyzt scans of eGFP expressing astrocytes during ammonia neurotoxicity reveals no astrocyte swelling, only transient shrinkage. Representative images are shown below. Red outline represents volume at time 0. Scale bar represents 5 µm. ***P<0.001, n=12 for each group, unpaired t test. FIG. 2L is a diagram illustrating how excess ammonia might anatomically (via end-feet, e.f.) and enzymatically (via glutamine synthetase, GS, trapped as glutamine, Gln) be drawn into astrocytes compromising their ability to buffer potassium. Data are shown as mean±SEM.

In FIG. 3A (top panel), cortical slices from wild-type mice (>P21) were superfused with 7 mM NH$_4$Cl. In FIG. 3A (bottom panel), representative ISM recordings for [NH$_4^+$]$_o$ and [K$^+$]$_o$ illustrating similar ionic changes observed in vivo. In FIG. 3B, mean Δ[ion]$_o$ were recorded following ammonia superfusion. [NH$_4^+$]$_o$ (n=9) and [K$^+$]$_o$ (n=18). In FIG. 3C, representative whole-cell recordings show that ammonia reduces the chloride current induced by ramp voltage with application of GABA. In FIG. 3D, ammonia causes a right shift of the I-V curve, which is prevented by NKCC1 antagonist bumetanide (BUM). In FIG. 3E, bumetanide prevented ammonia-induced depolarization of $E_{GABA}$. **P=0.0034, n=11 (control), 11 (NH$_4$Cl), 7 (BUM), 7 (NH$_4$Cl+BUM), Wilcox on signed ranks test. In FIGS. 3F and 3G, gramicidin perforated patch recordings with ramp voltage demonstrate that NKCC1 deletion (Slc12a2$^{-/-}$) prevents the depolarizing right shift of the GABA I-V curve. In FIG. 3H, ammonia depolarized $E_{GABA}$ in wild-type (Slc12a2$^{+/+}$), but not knock-out (Slc12a2$^{-/-}$) mice. In FIG. 3I, an immunofluorescence micrograph of adult Otc$^{spf-ash}$ and wild-type mouse cortex labeled with primary antibody against NKCC1 and DAPI-stained nuclei is shown. Scale bar represents 100 µm. Inset shows NKCC1 labeling in choroid plexus (positive control). Scale bar represents 250 lam. FIG. 3J is a diagram showing the proposed mechanism for ammonia neurotoxicity. NH$_4^+$ competes with [K$^+$] ions for active uptake, impairing astrocyte potassium buffering. This leads to an increase in [K$^+$]$_o$, over activating neuronal NKCC1, which depolarizes $E_{GABA}$ rendering GABAergic (inhibitory) neurotransmission less effective. Na$^+$—K$^+$-ATPase (NKA), glutamate (Glu), glutamine synthetase (GS), glutamine (Gln), Na$^+$—K$^+$-2Cl$^-$ cotransporter isoform 1 (NKCC1), GABA$_A$ receptor (GABA$_A$R), K$^+$—Cl$^-$ cotransporter isoform 2 (KCC2), bumetanide (BUM), membrane potential ($V_m$), GABA reversal potential ($E_{GABA}$). Data are shown as mean±SEM.

In FIG. 4A, awake mice were treated with systemic NH$_4$Cl (7.5 mmol kg$^{-1}$), cortical NH$_4$Cl (10 mM), or cortical KCl (12.5 mM)±bumetanide (30 mg kg$^{-1}$ i.p. or 5 µM cortically), while electrophysiological and behavioral changes were recorded. FIG. 4B shows 10 consecutive sweeps of field excitatory post-synaptic potentials (fEPSP) elicited by paired-pulse whisker stimulation before, during, and after cortical application of NH$_4$Cl with (blue box). In FIG. 4C, the facilitating (increased) paired-pulse ratio (PPR) induced by NH$_4$Cl cortical application (blue box) is reversed by bumetanide. *P<0.001, n=10 for both groups, unpaired t test. In FIG. 4D, the PPR facilitation seen following KCl cortical application (blue box) is similarly reduced by bumetanide. P=0.0022, n=6 (KCl) and 5 (KCl+BUM), Mann-Whitney U test. In FIG. 4E, bumetanide improves spontaneous mouse movement after a systemic NH$_4$Cl load (blue box) in Otc$^{spf-ash}$ mice. P<0.01, n=8 (NH$_4$Cl) and 7 (NH$_4$Cl+ BUM), Mann-Whitney U test. In FIG. 4F, following a systemic NH$_4$Cl load in Otc$^{spf-ash}$ mice, sensory-motor phenotype score was reduced by bumetanide treatment. P<0.01, n=8 (NH$_4$Cl) and 7 (NH$_4$Cl+BUM), Mann-Whitney U test. In FIG. 4G, frequency of myoclonic events induced by ammonia and/or potassium is reduced by bumetanide treatment. *P<0.001, P<0.01, n=10 (systemic NH$_4$Cl), 10 (cortical NH$_4$Cl) and 6 (cortical KCl). Mann-Whitney U test. FIG. 4H shows a cox regression analysis of Otc$^{spf-ash}$ mouse survival time after a NH$_4$Cl overdose (10 mmol kg$^{-1}$). *P=0.021, n=9 (NH$_4$Cl) and 10 (NH$_4$Cl+ bumetanide). Data is shown as mean±SEM.

FIGS. 5A and 5B show ammonia levels in blood plasma and brain before and after 7.5 mmol kg$^{-1}$ NH$_4$Cl. ***P<0.001, n=7 for each group, Mann-Whitney U test. FIGS. 5C and 5D show cortical [NH$_4^+$]$_o$ increase and phenotype score in NH$_4$Cl and NH$_4$Ac injected mice. P=0.88, n=7 (NH$_4$Cl) and 5 (NH$_4$Ac), Mann-Whitney U test. FIGS. 5E, 5F, and 5G show Otc$^{spf-ash}$ and WT mouse freezing behavior upon testing for learning impairment after training for 4 days. *P<0.01. In FIG. 5H, double-barreled ion-sensitive microelectrodes (ISM), electroencephalogram (EEG) and electromyogram (EMG) electrodes were used to record seizure activity during acute ammonia neurotoxicity in awake mice. The ammonia was either applied systemically (7.5 mmol kg$^{-1}$) or cortically (10 mM), and EEG electrodes were placed in both cortex (Ctx) and thalamus (Tha). Figure SI depicts representative EEG and EMG trace showing myoclonic seizures in and during NH$_4$Cl cortical superfusion. In FIG. 5J, local field recordings demonstrate that poly-spike-and-wave discharges in the cortex (Ctx) precede those in the thalamus (Tha) in systemic and cortical ammonia exposure. n=478 events, 6 mice. Data are shown as mean±SEM.

FIG. 6A shows [K$^+$]$_o$ increase following ammonia injection in Otc$^{spf-ash}$ and WT littermates. ***P<0.001, n=10 (Otc$^{spf-ash}$) and 5 (WT), Mann-Whitney U test. FIG. 6B is a scatterplot of [NH$_4^+$]$_o$ increase following ammonia (7.5 mmol kg$^{-1}$) or saline administration (red box). n=7 for each group. Red arrow indicates mean onset of seizures. FIG. 6C is a scatterplot of [K$^+$]$_o$ increase following ammonia (7.5 mmol kg') or saline administration (red box). n=10 (ammonia) and 7 (control). FIG. 6D is a scatterplot of [NH$_4^+$]$_o$ increase following cortical application of ammonia (10 mM, red box). n=4. FIG. 6E is a line graph showing that cortical application of 12.5 mM KCl replicates the cortical [K$^+$]$_o$ increase seen following 10 mM NH$_4$Cl application at different depths in the brain. n=5 for each depth. FIG. 6F shows that ammonia-induced pH effects are mild and delayed. Linear regression of seizure frequency on pH$_o$ is shown. Otc$^{spf-ash}$ mice show a mild extracellular brain alkalinization and peripheral (blood) acidosis, following 7.5 mmol kg' ammonia i.p. Both pH changes correlate weakly with seizure frequency. Data are shown as mean±SEM.

In FIG. 7A, representative $^1$H-NMR spectra 30 minutes after injection with saline or ammonia in Otc$^{spf-ash}$ mice is shown. ppm (parts per million), aspartate (Asp), glutamine (Gln), glutamate (Glu), γ-aminobutyric acid (GABA), glutamine+glutamate (Glx), N-acetylaspartic acid (NAA), N-acetylaspartylglutamate (NAAG), alanine (Ala), lactate (Lac). In FIG. 7B, brain [glutamine] measured by $^1$H-NMR 30 minutes after saline (ctrl) or ammonia is shown. *P=0.015, n=6 for each group, Kruskall-Wallis test. FIG. 7C shows $[NH_4^+]_o$ at different depths in the brain during direct cortical application of ammonia. The ammonia gradient in the brain dissipates when glutamine synthetase is inhibited with 1.5 mM MSO. Depth 0 µm represents ISM in the solution. *P=0.019, **P<0.01, n=5 for each depth, Mann-Whitney U test. In FIG. 7D, glutamine synthetase inhibition further compromises potassium buffering by preventing ammonia removal in astrocytes. $[NH_4^+]_o$ increase following ammonia±L-methionine sulfoximine (MSO) (0.83 mmol kg', administered 3 hours before the ammonia) i.p. in $Otc^{spf\text{-}ash}$ mice. *P=0.0043, **P=0.048, n=6 (Ctrl), 6 (MSO), 7 ($NH_4Cl$) and 5 ($NH_4Cl$+MSO), Mann-Whitney U test. FIG. 7E shows $[K^+]_o$ increase following ammonia injection and/or MSO in $Otc^{spf\text{-}ash}$ mice. *P=0.0016, **P=0.013, n=9 (Ctrl), 6 (MSO), 10 ($NH_4Cl$) and 5 ($NH_4Cl$+MSO), Mann-Whitney U test. In FIG. 7F, inhibiting GS with MSO (0.83 mmol kg$^{-1}$ i.p.) induces ME in awake mice. The ME phenotype was exacerbated when ammonia is co-administered. *P=0.00022, n=7 (MSO), 22 ($NH_4Cl$) and 7 ($NH_4Cl$+MSO), Kruskall-Wallis test. In FIG. 7G, ammonia causes a variable reduction in the potassium uptake of neurons. $Na^+$—$K^+$-ATPase-dependent (ouabain-sensitive) uptake of potassium analogue $^{86}Rb^+$ in cultured neurons, normalized to vehicle (0 mM $NH_4Cl$). *P<0.0001, n=20 (0 mM), n=4 (0.5 mM), n=4 (2 mM), n=16 (5 mM), n=4 (10 mM), Kruskall-Wallis test. Data are shown as mean±SEM.

In FIG. 8A, for awake calcium imaging change in rhod-2 flourescence ($\Delta F/F_0$) was normalized to eGFP to reduce movement artifacts. Calcium transients were defined as $\Delta F/F_0 > 2$ standard deviations (a) from baseline. In FIG. 8B, increased calcium activity is an early sign of ammonia neurotoxicity, but calcium activity paradoxically decreases during the period with peak ME frequency, before increasing again. Red box indicates time of i.p. injection. Heat bar indicates mean ME frequency per minute. ***P<0.0001, n=52 (ammonia) and 62 (control) cells sampled from 12 animals, unpaired t test with Bonferroni correction. In FIG. 8C, Pearson correlation of astrocyte calcium transients (cell) and ECoG seizure recordings is shown. n=52 cells. FIG. 8D depicts that representative calcium ($\Delta F/F_0$) and corresponding EEG trace demonstrate a weak temporal correlation between individual myoclonic events (ME) and calcium transients (coefficient<0.3). In FIG. 8E, ammonia injection desynchronizes calcium transients, as assessed by Pearson correlation of $\Delta F/F_0$. *P<0.0001, n=52 (ammonia) and 62 (control) cells, paired t test. FIG. 8F shows volume analysis of texas red hydrazide (TxR) loaded astrocytes in cortical slices. In the left panel, texas red selectively labels astrocytes expressing eGFP under the Glt-1 promoter. Scale bar represents 10 µm. Right panel, 10 mM $NH_4Cl$ is not associated with acute astrocyte swelling, which was only observed in conjunction with cell lysis when 50 mM $NH_4Cl$ was applied. P=0.0019 (50 mM $NH_4Cl$ vs. Ctrl), n=13 (Control), 12 (10 mM), 10 (50 mM), unpaired t test. In FIG. 8G, seizure frequency and phenotype score in wild-type (WT) and $Aqp4^{-/-}$ mice injected with 7.5 mmol kg$^{-1}$ $NH_4Cl$ i.p. P=0.829 (seizures), P=0.357 (encephalopathy), n=10 (ctrl) and 9 ($Aqp4^{-/-}$), Mann-Whitney U test. FIG. 8H shows cortical $[NH_4^+]_o$ in WT and $Aqp4^{-/-}$ mice before and after ammonia injection. P=0.94, n=6 for each group, Mann-Whitney U test. In FIG. 8I, brain water content measured by wet-to-dry ratios in control and ammonia injected WT and $Aqp4^{-/-}$ mice is shown. Ammonia injection does not cause increased brain water content. $Aqp4^{-/-}$ mice have increased brain water content in the control setting as has been described previously (Butterworth, R. F., "Pathophysiology of Hepatic Encephalopathy: A New Look at Ammonia," Metab. Brain Dis. 17:221-227 (2002), which is hereby incorporated by reference in its entirety). P=0.59 (WT), P=0.69 ($Aqp4^{-/-}$), n=10 (WT ctrl), 5 (WT $NH_4Cl$), 5 ($Aqp4^{-/-}$ ctrl) and 5 ($Aqp4^{-/-}$ $NH_4Cl$), Mann-Whitney U test. In FIG. 8J, brain water content is not increased 30 minutes after mild to moderate ammonia intoxication, but is elevated when a lethal dose is administered. P=0.0025, n.s.=not significant, n=7 (0 mmol kg$^{-1}$), 5 (5 mmol kg$^{-1}$), 6 (7.5 mmol kg$^{-1}$), 5 (10 mmol kg$^{-1}$), Mann-Whitney U test. In FIG. 8K, no significant change in global hemodynamic parameters in the present model of acute ammonia neurotoxicity was found (cerebral perfusion pressure: CPP, cerebral bloodflow: CBF and intracranial pressure: ICP). Data are shown as mean±SEM.

In FIG. 9A, representative traces show that bicuculline blocks the current induced by ramp voltage after GABA application. In FIG. 9B, the I-V curve shows that bicuculline blocks all GABA-induced current.

In FIGS. 10A and 10B, 10 consecutive sweeps and quantitation following paired-pulse whisker stimulation shows KCl superfusion (12.5 mM, blue box) no longer evokes a facilitating sensory response (disinhibition) when co-administered with bumetanide (BUM, 5 µM). **P<0.001. FIG. 10C shows an increase in cortical $[K^+]_o$ following a systemic $NH_4Cl$ load in $Otc^{spf\text{-}ash}$ mice that is unchanged by bumetanide. In FIG. 10D, an increase in cortical $[K^+]_o$ following a cortical $NH_4Cl$ is unchanged by bumetanide. Data are shown as mean±SEM.

DETAILED DESCRIPTION OF THE INVENTION

Figures 1A, 1B, 1C, 1D:
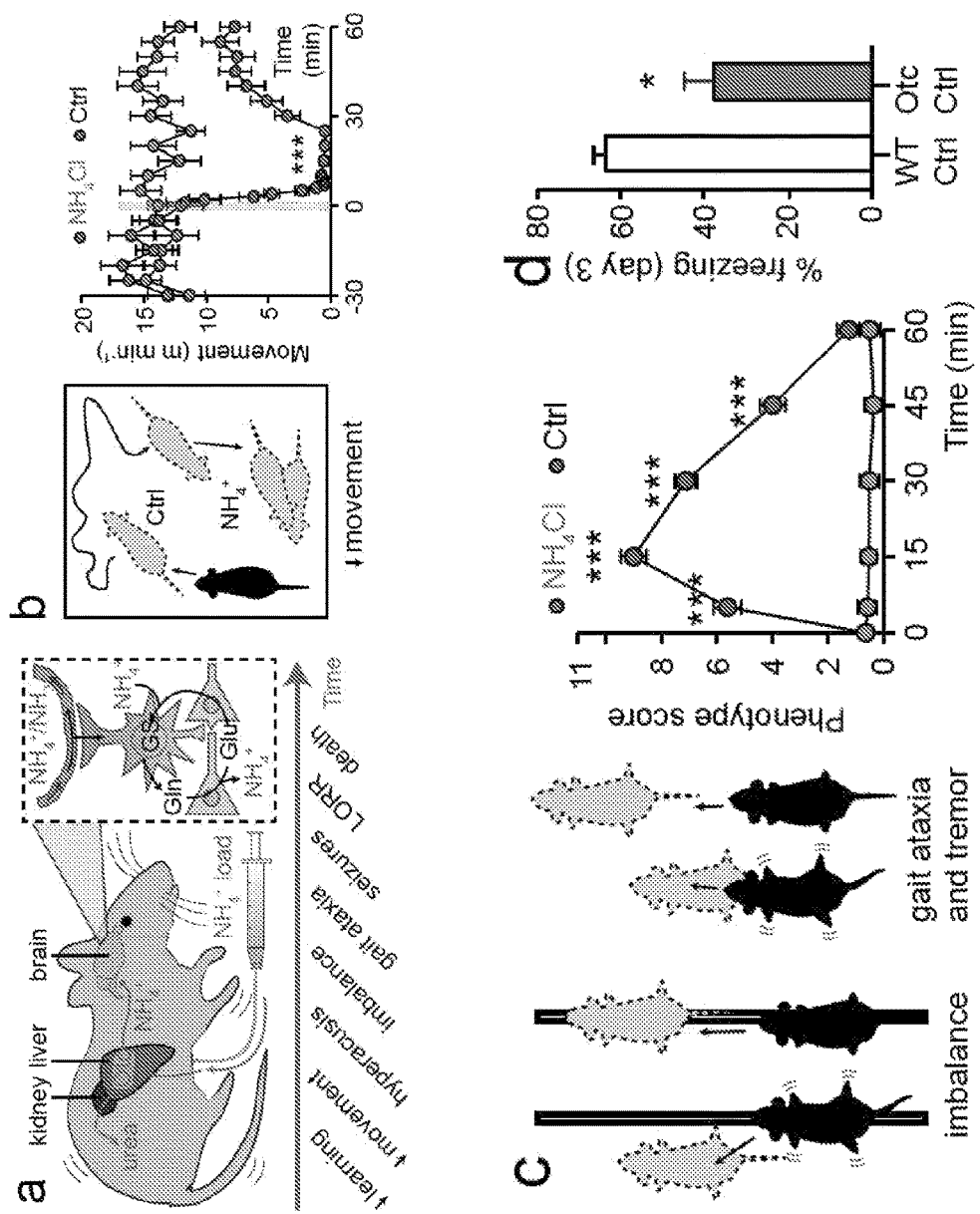
FIGS. 1A-1I illustrate that acute ammonia neurotoxicity is characterized by severe neurological impairment and cortical disinhibition.

A first aspect of the present invention relates to a method of treating or preventing brain impairment in a subject. The method includes selecting a subject having or susceptible of having ammonia neurotoxicity and administering a $Na^+$—$K^+$-2$Cl^-$ cotransporter isoform 1 ("NKCC1") inhibitor to the selected subject under conditions effective to treat or prevent brain impairment.

In absorptive and secretory epithelia, transcellular ion transport depends on specific plasma membrane proteins for mediating ion entry into and exit from cells. In the basolateral membrane of almost all epithelia, sodium exit and potassium entrance occur through $Na^+K^+$-ATPase, generating electrochemical gradients that constitute a driving force for $Na^+$ influx and $K^+$ efflux. Transport of these ions following their gradients can be accomplished by specific ion channels, allowing membrane passage of ions alone or by transporters in which $Na^+$ or $K^+$ transport is accompanied by other ions or solutes by means of several different solute transporters. These membrane proteins are known as secondary transporters because ion or molecule translocation is not dependent on ATP hydrolysis but rather on gradients generated by primary transporters. A secondary transport mechanism that is very active in transcellular ion transport in epithelial cells is one in which cations ($Na^+$ or $K^+$ are coupled with chloride, with a stoichiometry of 1:1; therefore, ion translocation produces no change in transmembrane potential. For this reason, these transporters are known as electroneutral cation-Cl⁻ coupled cotransporters. In addition to being heavily implicated in ion absorptive and secretory mechanisms, electroneutral cation-Cl⁻ coupled cotransporters play a key role in maintenance and regulation of cell volume in both epithelial and nonepithelial cells. Because Na⁺ influx and K⁺ efflux by electroneutral cotransporters are rapidly corrected by Na⁺K⁺-ATPase, the net effect of its activity is Cl movement inside or outside cells. This is known to be accompanied by changes in cell volume. A variety of new physiological roles for electroneutral cotransporters are emerging (e.g., regulation of intraneuronal Cl⁻ concentration and thus modulation of neurotransmission.) Gamba, "Molecular Physiology and Pathophysiology of Electroneutral Cation-Chloride Cotransporters." *Physiol. Rev.* 85: 423-493 (2005); U.S. Patent Publication No. 2012/0004225 to Wanaski et al., both of which are hereby incorporated by reference in their entirety.

Four groups of electroneutral cotransporter systems (also known as "symporters") have been functionally identified based on cation(s) coupled with chloride, stoichiometry of transport process, and sensitivity to inhibitors. These systems include: (1) the benzothiadiazine (or thiazide)-sensitive Na⁺Cl⁻ cotransporter; (2) the sulfamoylbenzoic (or bumetanide) sensitive Na⁺K⁺2 Cl⁻ cotransporters; (3) the sulfamoylbenzoic (or bumetanide) sensitive Na⁺Cl⁻ cotransporters; and (4) the dihydroindenyloxy-alkanoic acid (DIOA)-sensitive K⁺Cl⁻ cotransporter. The present invention relates to the use of sulfamoylbenzoic (or bumetanide) sensitive Na⁺K⁺2Cl⁻ cotransporters, and more specifically, NKCC1 inhibitors. Physiological evidence for these transport mechanisms became available at the beginning of the 1980s, and a remarkable amount of information was generated in the following years by characterizing these transport systems in many different cells and experimental conditions. Gamba, "Molecular Physiology and Pathophysiology of Electroneutral Cation-Chloride Cotransporters." *Physiol. Rev.* 85: 423-493 (2005); U.S. Patent Publication No. 2012/0004225 to Wanaski et al., both of which are hereby incorporated by reference in their entirety.

NKCC1 is widely distributed throughout the body and transports sodium, potassium, and chloride into the cell. NKCC1 is also found throughout the nervous system. Lenart et al., "Na—K—Cl Cotransporter-Mediated Intracellular Na⁺ Accumulation Affects Ca²⁺ Signaling in Astrocytes in an In Vitro Ischemic Model," *The Journal of Neuroscience* 24(43): 9585-9597 (2004); U.S. Patent Publication No. 2012/0004225 to Wanaski et al., both of which are hereby incorporated by reference in their entirety. The regulation of Cl⁻ transport into and out of cells plays a critical role in the maintenance of intracellular volume, as described supra, and the excitability of GABA responsive neurons regulated by at least two ion cotransporters: CF influx is mediated by the NKCC1 which mediates the Cl⁻ influx and KCC1 or KCC2 which mediates the Cl⁻ efflux. Kahle et al., "WNK3 Modulates Transport of Cl⁻ In and Out of Cells: Implications for Control of Cell Volume and Neuronal Excitability," *Proc. Natl. Acad. Sci. U.S.A.* 102(46): 16783-16788 (2004), which is hereby incorporated by reference in its entirety.

The maintenance of intra- and extracellular electrolyte homeostasis is required for a wide range of essential physiologic processes, including general functions (e.g., maintenance of proper cell volume), specialized cell functions (e.g., control of neuronal excitability), and global functions (e.g., regulation of blood pressure). This homeostasis is achieved via the regulated movement of Na⁺, K⁺, and Cl⁻ across cell membranes by ion channels, cotransporters, exchangers, and pumps that execute transmembrane electrolyte flux. Kahle et al., "WNK3 Modulates Transport of Cl- In and Out of Cells: Implications for Control of Cell Volume and Neuronal Excitability," *Proc. Natl. Acad. Sci. U.S.A.* 102(46): 16783-16788 (2004); U.S. Patent Publication No. 2012/0004225 to Wanaski et al., both of which are hereby incorporated by reference in their entirety.

The predominant mechanism by which intracellular volume is maintained in cells in response to changes in extracellular tonicity is the raising or lowering of intracellular Cl⁻ concentration ($[Cl^-]_i$), thereby minimizing transmembrane water flux. $[Cl^-]_i$ is modulated by altering the balance between Cl⁻ entry and exit. The major mediator of Cl⁻ entry is NKCC1 and Cl⁻ exit is largely mediated by KCC1. These cotransporters are both regulated by extracellular tonicity: hypertonicity activates NKCC1 and inhibits KCC1, whereas hypotonicity has the opposite effect. Kahle et al., "WNK3 Modulates Transport of Cl⁻ In and Out of Cells: Implications for Control of Cell Volume and Neuronal Excitability," *Proc. Natl. Acad. Sci. U.S.A.* 102(46): 16783-16788 (2004); U.S. Patent Publication No. 2012/0004225 to Wanaski et al., both of which are hereby incorporated by reference in their entirety.

An analogous system plays a key role in the control of neuronal excitability. In the adult brain, GABA is the major inhibitory neurotransmitter. If [Cl⁻], is below its equilibrium potential, Cl⁻ enters the cell, resulting in hyperpolarization and inhibition. If $[Cl^-]_i$ is above its equilibrium potential, GABA induces Cl⁻ efflux, depolarization, and neuronal excitation. The importance of $[Cl^-]_i$ regulation has been recognized with the discovery that GABA neurotransmission is not uniformly inhibitory; it is predominantly excitatory in the neonatal period. Similarly, neurons of the suprachiasmatic nucleus show circadian variation in their response to GABA, demonstrating the ability to dynamically regulate $[Cl^-]_i$. GABA neurotransmission in the peripheral nervous system is predominantly excitatory. Variation in $[Cl^-]_i$ in these neurons is determined by mechanisms highly similar to those governing cell volume. Cl⁻ influx largely occurs via NKCC1. Kahle et al., "WNK3 Modulates Transport of Cl⁻ In and Out of Cells: Implications for Control of Cell Volume and Neuronal Excitability," *Proc. Natl. Acad. Sci. U.S.A.* 102(46): 16783-16788 (2004); U.S. Patent Publication No. 2012/0004225 to Wanaski et al., both of which are hereby incorporated by reference in their entirety. For a review of NKCC1 structure, function and regulation, see Haas and Forbush, "The Na—K—Cl Cotransporter of Secretory Epithelia," *Annu. Rev. Physiol.* 62:515-534 (2000), which is hereby incorporated by reference in its entirety.

The NKCC1 inhibitors of the present invention described herein may be used for the regulation, including prevention, management, and treatment, of a range of brain impairments including, but not limited to disorders that involve at least one Na⁺—K⁺-2Cl⁻ cotransporter. Embodiments of the present invention encompass compounds described herein which modulate, regulate, inhibit, stimulate, activate, and/or bind to electroneutral cation-chloride cotransporters including but not limited to basolateral bumetanide-sensitive NKCC1 cotransporters.

NKCC1 inhibitors that may be effectively employed in the inventive methods are capable of reducing the effective amount, inactivating, and/or inhibiting the activity of a NKCC1 cotransporter. Preferably such compositions are capable of reducing the effective amount, inactivating, and/or inhibiting the activity of the cotransporter NKCC1. In certain embodiments, the inventive compositions comprise at least one treatment agent selected from antagonists of NKCC1 (including but not limited to, small molecule inhibitors of NKCC1, antibodies, or antigen-binding fragments thereof, that specifically bind to NKCC1 and soluble NKCC1 ligands); anti-sense oligonucleotides to NKCC1; NKCC1-specific small interfering RNA molecules (siRNA or RNAi); and engineered soluble NKCC1 molecules. NKCC1 inhibitors of the present invention include, but are not limited to, loop diuretics (i.e., diuretics which inhibit the $Na^+$—$K^+$-$2Cl^-$ cotransporter in the ascending limb of the loop of Henle and thereby inhibit the reabsorption of sodium, potassium, and chloride ions).

In one embodiment, the agent is selected from the group consisting of NKCC1 inhibitors such as bumetanide, furosemide, piretanide, azosemide, ethacrynic acid, torsemide, muzolimine, tripamide, and etozolin, and analogs and functional derivatives of such compounds. A most preferred NKCC1 inhibitor to be used in the present invention is bumetanide, which has the following structure:

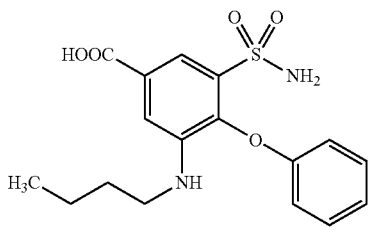 [SMILES: CCCCNc1cc(C(=O)O)cc(S(N)(=O)=O)c1Oc1ccccc1]

See U.S. Pat. No. 3,806,534 to Feit et al.; THE MERCK INDEX: AN ENCYCLOPEDIA OF CHEMICALS, DRUGS, AND BIOLOGICALS 1485 (Maryadele J. O'Neil et al., eds., Merck Research Laboratories 2006) (1889), both of which are hereby incorporated by reference in their entirety. Bumetanide is a specific inhibitor of NKCC1 that is routinely used in clinical practice to treat fluid retention, with a favorable side-effect profile. Hannaert et al., "Rat NKCC2/NKCC1 Cotransporter Selectivity For Loop Diuretic Drugs," *Naunyn Schmiedebergs Arch. Pharmacol.* 365:193-199 (2002), which is hereby incorporated by reference in its entirety. For additional NKCC1 inhibitors, see U.S. Pat. No. 3,665,002 to Popelak et al.; U.S. Pat. No. 3,255,241 to Schultz et al.; U.S. Pat. No. 3,058,882 to Stürm et al.; U.S. Pat. No. 4,010,273 to Bormann et al.; and U.S. Pat. No. 4,018,929 to Delarge et al., all of which are hereby incorporated by reference in their entirety.

Exemplary brain impairments that may cause ammonia neurotoxicity (i.e., hyperammonemia), or make a subject susceptible of having ammonia neurotoxicity (i.e., hyperammonemia), and that may be prevented or treated in the present invention include, but are not limited to, conditions of neurological dysfunction such as encephalopathy, epileptic seizures, ataxia, coma, addictive disorders, Alzheimer's Disease, anxiety disorders, autism, bipolar disorder, cancer, cerebral edema, depression, diabetes, head trauma, hepatic diseases, Huntington's Disease, insomnia, ischemia, meningitis, migraine, neuropathic pain, nociceptive pain, ocular diseases, Parkinson's Disease, personality disorders, psychosis, schizophrenia, and stroke.

Epileptic seizures, in particular, may lead to ammonia neurotoxicity (i.e., hyperammonemia), and may be effectively prevented or treated by the methods of the present invention. In one embodiment, the NKCC1 inhibitor of the present invention reduces the incidence of epileptic seizures or, alternatively, reduces the spread of epileptic seizures. The NKCC1 inhibitors of the present invention may be administered to a subject after the subject has suffered from an epileptic seizure or, alternatively, prior to the suffering of an epileptic seizure, either before or after the subject has been diagnosed with epilepsy. Examples of types of seizures which the NKCC1 inhibitors of the present invention may prevent or treat include, but are not limited to, status epilepticus, petit mal, absence, myoclonic, clonic, tonic, tonic-clonic, and atonic seizures, acquired aphasia, acquired aphasia with epilepsy (Laundau-Kleffner syndrome), acquired epileptic aphasia, cortical dysplasia-focal epilepsy syndrome (CDFE), neonatal seizures, hippocampal sclerosis (HS) and hippocampal, cerebral, and cerebellar atrophy, and febrile seizures including complex febrile convulsions (CFC). In one particular embodiment, the epileptic seizure is a myoclonic seizure.

Encephalopathy may also lead to ammonia neurotoxicity (i.e., hyperammonemia), and may be effectively prevented or treated by the methods of the present invention. In one embodiment, the NKCC1 inhibitor treats or prevents encephalopathy. The NKCC1 inhibitors of the present invention may be administered to a subject after the subject suffers from encephalopathy or prior to the onset of encephalopathy. Exemplary types of encephalopathy that may be prevented or treated by the NKCC1 inhibitors of the present invention include, but are not limited to, toxic encephalopathy, diabetic encephalopathy, hepatic encephalopathy, hypertensive encephalopathy, metabolic encephalopathy, uremic encephalopathy, liver diseases, disturbances of the water/electrolyte or acid/base balance, myoclonic infantile encephalopathy, infantile postictereca encephalopathy, postcombustional encephalopathy, encephalopathy caused by heavy metals, toxic encephalopathy caused by alcohol, bovine spongiform encephalopathy, supcortical progressive encephalopathy, and traumatic encephalopathy.

Hepatic encephalopathy, in particular, may lead to ammonia neurotoxicity (i.e., hyperammonemia) and may be effectively treated or prevented by the present invention. Hepatic encephalopathy is a syndrome associated with liver dysfunction, characterized by a decline in mental function and neurological abnormalities. Distinctive clinical signs include personality changes and intellectual impairment, and neuromuscular anomalies such as asterixis (flapping tremor) and alterations in gait. The syndrome typically manifests in patients with an extensive collateral blood vessel system (extrahepatic portal shunts) which diverts portal venous blood away from the liver into the systemic circulation. Thus, toxic metabolites absorbed into the bloodstream from the intestines may largely bypass the liver and enter the general circulatory system without being detoxified. Among other ramifications, such toxins can cause metabolic aberrations in the central nervous system which lead to increased permeability of the blood-brain barrier and increased transport of toxic substances across this barrier into the brain. In addition to promoting permeability of the neuronal membrane, high plasma levels of certain neurotoxins are thought to contribute to changes in energy metabolism and nerve processes in the brain. Ammonia is implicated in the pathogenesis of hepatic encephalopathy. U.S. Patent Publication No. 2007/0269403 to Halow, which is hereby incorporated by reference in its entirety.

The NKCC1 inhibitors of the present invention are effective in treating or preventing brain impairment in a subject that has or is susceptible of having ammonia neurotoxicity (i.e., hyperammonemia). Hyperammonemia is caused by ammonia that crosses the blood-brain barrier and rapidly saturates its only removal pathway, located in the astrocytes.

Ammonia is normally produced in the gastrointestinal tract by bacterial degradation of peptides and other nitrogen-containing compounds, and then detoxified in the liver by conversion to urea and glutamine. Under normal conditions, ammonia is produced by an amino group present on all amino acids. The α-amino group is a catabolic key that, when present, keeps amino acids safely locked away from oxidative breakdown. Removing the α-amino group is essential for producing energy from any amino acid. Under normal circumstances, both the liver and the brain generate ammonia in this removal process, contributing substantially to total body ammonia production. The urea cycle is completed in the liver, where urea is generated from free ammonia. U.S. Patent Publication No. 2005/0154032 to Lieberburg, which is hereby incorporated by reference in its entirety. If the liver is sufficiently diseased, or bypassed as when portal shunts are present, plasma levels of ammonia may increase to toxic levels, affecting, for example, the transport of amines, water, and electrolytes across the neuronal membrane. See U.S. Patent Publication No. 2007/0269403 to Halow, which is hereby incorporated by reference in its entirety.

Low-level synthesis of certain cycle intermediates in extra-hepatic tissues make a small contribution to waste nitrogen disposal as well. Two moles of waste nitrogen are eliminated with each mole of urea excreted. A portion of the cycle is mitochondrial in nature. Thus, mitochondrial dysfunction may impair urea production and result in hyperammonemia. Overall, activity of the urea cycle is regulated by the rate of synthesis of N-acetylglutamate, the enzyme activator that initiates incorporation of ammonia into the cycle. U.S. Patent Publication No. 2005/0154032 to Lieberburg, which is hereby incorporated by reference in its entirety.

The brain must expend energy to detoxify and export the ammonia it produces. This is accomplished in the process of producing adenosine diphosphate (ADP) from adenosine triphosphate (ATP) by the enzyme glutamine synthetase, which is responsible for mediating the formation of glutamine from an amino group. Synthesis of glutamine also reduces the total free ammonia circulating in the blood. Therefore, a significant increase in blood glutamine concentration can signal hyperammonemia. U.S. Patent Publication No. 2005/0154032 to Lieberburg, which is hereby incorporated by reference in its entirety.

The central nervous system is most sensitive to the toxic effects of ammonia. Many metabolic derangements occur as a consequence of high ammonia levels, including alteration of metabolism of important compounds such as pyruvate, lactate, glycogen, and glucose. High ammonia also induces changes in N-methyl-D-aspartate (NMDA) and gamma-aminobutyric acid (GABA) receptors, and it causes down-regulation in astroglial glutamate transporter molecules. As ammonia exceeds a normal concentration, an increased disturbance of neurotransmission and synthesis of both GABA and glutamine occurs in the central nervous system. The pathophysiology of hyperammonemia is primarily that of a central nervous system toxin that causes irritability, somnolence, vomiting, cerebral edema, and coma (altered consciousness) leading to death. In some cases, a patient's plasma ammonia levels may be elevated without causing abnormal mental status in that individual. U.S. Patent Publication No. 2005/0154032 to Lieberburg, which is hereby incorporated by reference in its entirety.

Progressive hyperammonemia, whether treated or not, eventually causes cerebral edema, coma, and death. Neurological symptoms include poor coordination, dysdiadochokinesia, hypotonia or hypertonia, ataxia, tremor, seizures, lethargy progressing to combativeness to obtundation to coma, and decorticate or decerebrate posturing. While the vast majority of morbidity associated with hyperammonemia derives from the primary cause, repeated hyperammonemic episodes also can cause morbidity. The result, given the direct toxicity of ammonia on the central nervous system, is a progressive decrease in intellectual function. U.S. Patent Publication No. 2005/0154032 to Lieberburg, which is hereby incorporated by reference in its entirety.

Hyperammonemia is frequently found in patients with serious liver diseases such as fulminant hepatitis, subacute hepatitis, and terminal stage liver cirrhosis. The psychoneurological syndrome observed in those patients with liver disease is known as hepatic encephalopathy, as described supra, and it is generally acknowledged that an elevated blood ammonia level is closely associated with its pathophysiology. See U.S. Pat. No. 4,996,236 to Nakamura, which is hereby incorporated by reference in its entirety.

By the terms "treating" or "treatment" of a brain impairment, it is intended that the severity of the impairment or the symptoms of the impairment are reduced, or the impairment is partially or entirely eliminated, as compared to that which would occur in the absence of treatment. Treatment does not require the achievement of a complete cure of the brain impairment. By the terms "preventing" or "prevention" of the brain impairment, it is intended that the inventive methods eliminate or reduce the incidence or onset of the impairment, as compared to that which would occur in the absence of treatment. Alternatively stated, the present methods slow, delay, control, or decrease the likelihood or probability of the impairment in the subject, as compared to that which would occur in the absence of treatment.

Subjects suitable for treatment according to the present invention include, but are not limited to, avian and mammalian subjects, and are preferably mammalian. Mammals of the present invention include, but are not limited to, canines, felines, bovines, caprines, equines, ovines, porcines, rodents (e.g., rats and mice), lagomorphs, primates, humans, and the like, and mammals in utero. Any mammalian subject in need of being treated or in need of prevention according to the present invention is suitable. Human subjects are preferred. Human subjects of both genders and at any stage of development (i.e., neonate, infant, juvenile, adolescent, and adult) can be treated according to the present invention. Particularly susceptible subjects include infants and juveniles, as well as adults. In the context of administering a NKCC1 inhibitor of the invention for purposes of treating brain impairment in a subject, the target subject population encompasses any subject with any brain impairment described herein. Particularly suitable subjects include those with epilepsy or those with encephalopathy. In one embodiment of the present invention, the NKCC1 inhibitor may be used to prevent or treat chronic hyperammonemia, particularly in juveniles or infants. In another embodiment, juveniles or infants having hyperammonemia or being susceptible to having hyperammonemia may have a congenital enzyme deficiency such as, but not limited to, alkaptonuria, essential fructosuria, hereditary fructose intolerance, galactosemia, adenosine deaminase deficiency, and lesch-nyhan syndrome.

In one embodiment of the present invention, the NKCC1 inhibitor used reduces accumulation of potassium surrounding astrocytes. Astrocytes were historically viewed as passive support cells, and were thought to perform important but perfunctory housekeeping tasks to optimize the environment for neural transmission. Recent evidence has challenged this concept by demonstrating that astrocytes can actively modulate neuronal function. Indeed, astrocytes are required for synapse formation and stability and can actively modulate synaptic transmission by release of glutamate by exocytosis (Volterra et al., "Astrocytes, From Brain Glue to Communication Elements: The Revolution Continues," *Nat. Rev. Neurosci.* 6(8):626-640 (2005); Haydon, P. G., "GLIA: Listening and Talking to the Synapse," *Nat. Rev. Neurosci.* 2(3):185-193 (2001), which are hereby incorporated by reference in their entirety). Astrocytes express several proteins that are required for exocytosis, and neurotoxins inhibit astrocytic glutamate release in cultures. Astrocytes also express functional vesicular glutamate transporters VGLUT 1/2 and pharmacological inhibition of VGLUT1/2 reduced $Ca^{2+}$-dependent glutamate release (Montana et al., "Vesicular Glutamate Transporter-Dependent Glutamate Release From Astrocytes," *J. Neurosci.* 24(12):2633-2642 (2004); Bezzi et al., "Astrocytes Contain a Vesicular Compartment That is Competent for Regulated Exocytosis of Glutamate," *Nat. Neurosci.* 7(6):613-620 (2004), which are hereby incorporated by reference in their entirety). However, other mechanisms by which astrocytes release glutamate likely exist, in addition, astrocytes possess multiple mechanisms for several key functions. For example, the important task of $K^+$ buffering is undertaken by several $K^+$ channels expressed by astrocytes, including KIR4.1 and rSlo K(Ca) (Price et al., "Distribution of rSlo Ca2+-Activated K+ Channels in Rat Astrocyte Perivascular Endfeet," *Brain Res.* 956(2):183-193 (2002), which is hereby incorporated by reference in its entirety), but also by the $K^+$—$Na^+$—$Cl^-$ cotransporter (Su et al., "Contribution of Na(+)-K(+)-Cl(-) Cotransporter to High-[K(+)](o)-Induced Swelling and EAA Release in Astrocytes," *Am. J. Physiol.* 282(5):C1136-Cl 146 (2002), which is hereby incorporated by reference in its entirety). See WO 2006/062683 to Nedergaard et al., which is hereby incorporated by reference in its entirety. The present invention utilizes these properties of astrocytes to treat and/or prevent brain impairment in a subject.

The NKCC1 inhibitors of the present invention may be used for the regulation, including prevention, prophylaxis, diagnosis, prognostication, management, and treatment, of a range of conditions that involve the depolarization of γ-aminobutyric acid reversal potential ($E_{GABA}$) including but not limited to the disorders described herein. In one embodiment of the present invention, the NKCC1 inhibitor prevents depolarization of γ-aminobutyric acid reversal potential ($E_{GABA}$).

Gamma-aminobutyric acid (GABA), the main inhibitory transmitter in the brain, principally exerts its rapid hyperpolarizing (inhibitory) action via anion-permeable $GABA_A$ receptors. Zhang et al., "Transition to Seizure: From 'Macro'- to 'Micro'-Mysteries," *Epilepsy Res.* 97:290-299 (2011), which is hereby incorporated by reference in its entirety. The minor "regulatory" E subunits of GABA are expressed in particular central nervous system locations such as the cortex, the substantia nigra, amygdala and hypothalamus whereas another minor subunit, it, is expressed outside the central nervous system in the uterus and breast tissue (overexpression of π has been observed in breast cancer). The "regulatory" subunit, γ, is a component of benzodiazepine-sensitive $GABA_A$ receptors. WO 2009/100040 to Shekdar et al., which is hereby incorporated by reference in its entirety.

Proper neural activity depends on maintaining an appropriate balance between excitation and inhibition. Any tipping of the balance too far toward inhibition leads to sedation, and conversely, tipping it too far toward excitation may trigger a seizure. For example, extrasynaptic δ subunit-containing $GABA_A$ receptors contribute to temporal lobe epilepsy by decreasing inhibitory input onto dentate granule cells and increasing the inhibition of inhibitory interneurons. Peng et al., "Altered Expression of the δ Subunit of the GABAA Receptor in a Mouse Model of Temporal Lobe Epilepsy," *J. Neurosci.* 24:8629-8639 (2004), which is hereby incorporated by reference in its entirety. This increase in the inhibition of the inhibitory interneurons tips the balance too far towards excitation by lessening the inhibitory signaling, leading to epileptic seizures.

Therapeutically effective amounts of NKCC1 inhibitors of the present invention can be determined in accordance with standard procedures, which take numerous factors into account, including, for example, the concentrations of these active agents in the composition, the mode and frequency of administration, the severity of the brain impairment condition to be treated (or prevented), and subject details, such as age, weight, overall health, and route of delivery. General guidance can be found, for example, in the publications of the International Conference on Harmonization and in REMINGTON'S PHARMACEUTICAL SCIENCES (Mack Publishing Company 1990), which is hereby incorporated by reference in its entirety. A clinician may administer NKCC1 inhibitors until a dosage is reached that provides the desired or required prophylactic or therapeutic effect. The progress of this therapy can be easily monitored by conventional assays. Therapeutically effective amounts of NKCC1 inhibitors may be, most preferably, 5 μM. Alternatively, a therapeutically effective amount of NKCC1 inhibitor may be more than 5 μM, such as but not limited to 6 μM, 7 μM, 8 μM, 9 μM, or 10 μM. Alternatively, a therapeutically effective amount of NKCC1 inhibitor may be less than 5 μM, such as but not limited to 4 μM, 3, μM, 2, μM, or 1 μM.

The NKCC1 inhibitors of the present invention can be administered alone or, optionally, as part of a combination therapy in conjunction with another active agent, depending upon the nature of the brain impairment that is being treated. Suitable second agents include those useful for the prevention and/or treatment of a range of brain impairments including, but not limited to, addictive disorders such as alcohol and narcotic addition, Alzheimer's Disease, anxiety disorders, autism, bipolar disorder, cancer, coma, cerebral edema, depression, diabetes, encephalopathy, epileptic seizures, head trauma, hepatic diseases, Huntington's Disease, insomnia, ischemia, meningitis, migraine, neuropathic pain, nociceptive pain, ocular diseases, Parkinson's Disease, personality disorders, psychosis, schizophrenia, and stroke. Accordingly, second agents for treatment in combination with NKCC1 inhibitors of the present invention include, but are not limited to, phenytoin, carbamazepine, barbiturates, phenobarbital, phenobarbital, mephobarbital, trimethadione, mephenytoin, paramethadione, phenthenylate, phenacemide, metharbital, benzchlorpropamide, phensuximide, primidone, methsuximide, ethotoin, aminoglutethinide, diazepam, clonazepam, clorazepate, fosphenytoin, ethosuximide, valproate, felbamate, gabapentin, lamotrigine, topiramate, vigrabatrin, tiagabine, zonisamide, clobazam, thiopental, midazolam, propofol, levetiracetam. oxcarbazepine, CCPene, GYK152466, serotonin receptor agonists, ergotamine, dihydroergotamine, sumatriptan, propranolol, metoprolol, atenolol, timolol, nadolol, nifeddipine, nimodipine, verapamil, aspirin, ketoprofen, tofenamic acid, mefenamic acid, naproxen, methysergide, paracetamol, clonidine, lisuride, iprazochrome, butalbital, benzodiazepines, divalproex sodium and other similar classes of compounds (U.S. Pat. No. 6,495,601 to Hochman and U.S. Patent Application Serial No. 2002/0082252 to Hochman, both of which are hereby incorporated by reference in their entirety). Additional active agents may include anti-infective agents, antibiotic agents, and antimicrobial agents. Representative anti-infective agents that may be useful in the present invention include vancomycin and lysostaphin. Representative antibiotic agents and antimicrobial agents that may be useful in the present invention include penicillinase-resistant penicillins, cephalosporins and carbapenems, including vancomycin, lysostaphin, penicillin G, ampicillin, oxacillin, nafcillin, cloxacillin, dicloxacillin, cephalothin, cefazolin, cephalexin, cephradine, cefamandole, cefoxitin, imipenem, meropenem, gentamycin, teicoplanin, lincomycin and clindamycin. Dosages of these antibiotics are well known in the art. See, e.g., MERCK MANUAL OF DIAGNOSIS AND THERAPY, Section 13, Ch. 157, 100$^{th}$ Ed. (Beers & Berkow, eds., 2004), which is hereby incorporated by reference in its entirety. The anti-inflammatory, anti-infective, antibiotic and/or antimicrobial agents may be combined prior to administration, or administered concurrently (as part of the same composition or by way of a different composition) or sequentially with the inventive therapeutic compositions of the present invention.

NKCC1 inhibitors of the present invention may be administered in a single dose, or in accordance with a multi-dosing protocol. In certain embodiments, the administering is repeated. For example, relatively few doses of the NKCC1 inhibitor may be administered, such as one or two doses. In other embodiments, the NKCC1 inhibitor may involve multiple doses over a period of days or weeks. The NKCC1 inhibitor can be taken one, two or three or more times daily for a period of time, such as for at least 5 days, 10 days or even 14 or more days. However, the different dosages, timing of dosages and relative amounts of the NKCC1 inhibitor can be selected and adjusted by one of ordinary skill in the art.

Compounds of the present invention can be administered by oral, inhalation, intranasal instillation, topical, transdermal, parenteral, subcutaneous, intravenous injection, intra-arterial injection, intramuscular injection, intraplurally, intraperitoneally, or by application by mucous membrane for prophylactic and/or therapeutic treatment. The most typical route of administration is subcutaneously although others can be equally effective. The next most common is intramuscular injection. This type of injection is most typically performed in the arm or leg muscles. Intravenous injections as well as intraperitoneal injections, intra-arterial, intracranial, or intradermal injections are also effective in preventing or treating brain impairment.

The agents of the present invention may be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the pharmaceutical agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

A second aspect of the present invention relates to a method of inhibiting accumulation of potassium surrounding astrocytes. The method includes contacting astrocytes with a NKCC1 inhibitor under conditions effective to inhibit accumulation of potassium surrounding the astrocytes.

In one embodiment, the method is carried out in vivo or, alternatively, in vitro. In another embodiment, the method comprises selecting a subject having or susceptible of having an accumulation of potassium surrounding astrocytes. A subject having or susceptible of having an accumulation of potassium surrounding astrocytes according to the present invention may include, but is not limited to, any subject that has or is susceptible of having any number of brain impairments described supra or, alternatively, ammonia neurotoxicity such as hyperammonemia. Therapeutically effective dosing of NKCC1 inhibitors related to this aspect of the invention is consistent with the aspect described supra.

A third aspect of the present invention relates to a method of maintaining astrocytic potassium buffering. The method includes contacting astrocytes with a NKCC1 inhibitor under conditions effective to maintain astrocytic potassium buffering.

In one embodiment, the method comprises selecting a subject requiring maintenance of astrocytic potassium buffering. A subject requiring maintenance of astrocytic potassium buffering according to the present invention may include, but is not limited to, any subject that has or is susceptible to having any number of brain impairments described supra or, alternatively, ammonia neurotoxicity such as hyperammonemia. Therapeutically effective dosing of NKCC1 inhibitors related to this aspect of the invention is consistent with the aspects described supra.

EXAMPLES

The following examples are provided to illustrate embodiments of the present invention but are by no means intended to limit its scope.

Example 1—Materials and Methods

Rodent Breeding and Behavioral Studies—All animal experiments were approved by the Animal Care and Use Committee of the University of Rochester. Otc$^{spf-ash}$ B6 C3-F1 mice and wild-type littermates were bred as described previously (see Ye et al. "Adenovirus-Mediated In Vivo Gene Transfer Rapidly Protects Ornithine Transcarbamylase-Deficient Mice From an Ammonium Challenge," *Pediatr. Res.* 41:527-535 (1997), which is hereby incorporated by reference in its entirety). Aqp4$^{-/-}$ mice and wild-type littermates were generated as described previously (Thrane et al., "Critical Role of Aquaporin-4 (AQP4) in Astrocytic Ca$^{2+}$ Signaling Events Elicited by Cerebral Edema," *Proc. Natl. Acad. Sci. U.S.A.* 108:846-851 (2010), which is hereby incorporated by reference in its entirety). Cortical slices were prepared from P21-30 C57BL/6J mice as outlined previously (Thrane et al., "Critical Role of Aquaporin-4 (AQP4) in Astrocytic Ca$^{2+}$ Signaling Events Elicited by Cerebral Edema," *Proc. Natl.* Acad. Sci. U.S.A. 108:846-851 (2010), which is hereby incorporated by reference in its entirety). Mice subjected to studies were males from 8 to 12 weeks of age.

Otc$^{spf-ash}$ mice were crossed with Glt-1-eGFP mice for imaging experiments. C57BL/6J mouse and Wistar rat pups were obtained from Jackson Laboratories. To analyze cognitive abilities in OTC mice, two commercial conditioning chambers (H10-11M-TC, Coulbourn Instruments) were adapted for contextual fear conditioning. Over the course of 4 days, mice were trained via a tone/shock protocol and trained to fear contextual and auditory cues. Better trained mice exhibited higher freezing percentages in the precesense of auditory or contextual cues (Anagnostaras et al., "Computer-Assisted Behavioral Assessment of Pavlovian Fear Conditioning in Mice," *Learning & Memory* (Cold Spring Harbor, N.Y.) 7:58-72 (2000); Wiltgen et al., "Memory for Context Becomes Less Specific With Time," *Learning & Memory* (Cold Spring Harbor, N.Y.) 14:313-317 (2007), both of which are hereby incorporated by reference in their entirety). Automated movement analysis was performed using AnyMaze™ software analysis of CCD-camera recordings in a standard mouse cage.

Animal Preparation for Awake In Vivo Recordings—Mouse preparation was modified from published protocols (Thrane et al., "Real-Time Analysis of Microglial Activation and Motility in Hepatic and Hyperammonemic Encephalopathy," *Neuroscience* 220:247-55 (2012); Dombeck et al., "Imaging Large-Scale Neural Activity With Cellular Resolution in Awake, Mobile Mice," *Neuron* 56:43-57 (2007), which are hereby incorporated by reference in their entirety). Briefly, mice were anesthetized using isoflurane (1.5% mixed with 1-2 L/min O$_2$), head restrained with a custom-made mini-frame, habituated over 2 days, a 1.5 mm craniotomy was opened over the somatosensory cortex, and the mice were allowed a 60 minute recovery prior to conducting the experiments. Body temperature was maintained with a heating pad. For systemic drug treatment, a polyethylene intraperitoneal (i.p.) catheter was surgically implanted to deliver drugs accurately and with minimal manipulation. For cortical drug application artificial cerebrospinal fluid (aCSF) was perfused across the cortex of awake mice at a rate of 2 mL/minute, into a custom-made well with ~200 µL volume, through tubing with ~100 µL volume, meaning the entire volume bathing the brain was exchanged approximately every 9 seconds. The aCSF solution contained (in mM) 126 NaCl, 2.5 KCl, 1.25 NaH$_2$PO$_4$, 2 MgCl$_2$, 2 CaCl$_2$, 10 glucose, and 26 NaHCO$_3$, pH 7.4. For imaging, calcium indicator rhod-2 AM (Invitrogen, 2 mM) was loaded onto exposed cortex for 45 minutes before applying agarose (1.5%, type III-A, Sigma) and a cover slip. Thrane et al., "Critical Role of Aquaporin-4 (AQP4) in Astrocytic Ca2+ Signaling Events Elicited by Cerebral Edema," *Proc. Natl. Acad. Sci. U.S.A.* 108:846-851 (2010), which is hereby incorporated by reference in its entirety.

Sensory-Motor Phenotype Score—A sensory-motor phenotype score was developed to quantify the severity of ammonia neurotoxicity based on two previous studies (Ye et al., "Adenovirus-Mediated In Vivo Gene Transfer Rapidly Protects Ornithine Transcarbamylase-Deficient Mice From an Ammonium Challenge," *Pediatr. Res.* 41:527-535 (1997); Guyenet et al, "A Simple Composite Phenotype Scoring System for Evaluating Mouse Models of Cerebellar Ataxia," *JoVE* (2010), both of which are hereby incorporated by reference in their entirety). Mouse movement and seizure activity were omitted from this score, because it was desired that these manifestations be independently and more quantitatively represented. The score thus consisted of four elements: hyperacusis (0-2), imbalance (0-3), ataxia/tremor (0-3) and level of consciousness (0-3). A maximum score of 11 represents deep coma (no corneal reflex) whilst 0 represents normal wakefulness. Each animal was scored after the first 5 minutes and then every 15 minutes as they progressed through the stereotypical stages of ammonia neurotoxicity. Hyperacusis was scored from 0 if the mouse did not display a startle response to 30-60 dB sound, 1 if the mouse responded to only 60 dB, and 2 if it responded to 30 dB as well. Imbalance was scored using a ledge test, and the mice were given 0 if they balanced on the ledge and let themselves down in a controlled fashion, 1 if they lost their footing whilst walking on the ledge, 2 if they did not effectively walk on or let themselves down from the ledge, and 3 if they were unable to walk, get down, or just fell off. Ataxia/tremor was scored using a gait test, where the mouse was encouraged to walk for a short distance. The mouse got 0 if it walked effectively, 1 if it had a slight tremor, 2 if it had a broad based gait or severe tremor, 3 if it dragged its abdomen on the ground or was unable to walk. Consciousness was scored as either 0 for awake, 1 loss of scatter reflex, 2 loss of righting reflex (LORR), 3 loss of corneal reflex.

Biochemical and Hemodynamic Analysis—Plasma ammonia analysis was performed on blood samples collected using 50 µL heparinized tubes from the femoral artery. A L-glutamate dehydrogenase based kit (Sigma) was used for the quantification of ammonia in plasma. For $^1$H-NMR, mouse forebrains were extracted, frozen, homogenized, and lyophilized before being reconstituted with D$_2$O as described previously (Zwingmann et al., "Selective Increase of Brain Lactate Synthesis in Experimental Acute Liver Failure: Results of a [1H-13C] Nuclear Magnetic Resonance Study," *Hepatology* 37:420-428 (2003), which is hereby incorporated by reference in its entirety). $^1$H-NMR spectra were acquired at 25° C. using a 600 mHz Varian Unity INOVA spectrometer (7200 Hz spectral width, 32 K data points, 64 signals averaged for each spectrum). For hemodynamic recordings an intracranial pressure probe (Millar) was inserted through a small 0.5 mm craniotomy over the somatosensory cortex. Cerebral blood flow was assessed using a fiber optic laser Doppler probe (PF5010, Perimed) and connected to an infrared laser doppler flow meter. Blood pressure was monitored through the femoral artery cannula (SYS-BP1, WPI), and cerebral perfusion pressure was deduced by subtracting ICP from blood pressure. All signals were digitized (Digidata 1332A, Axon Instruments) and analyzed (pClamp 10.2). Brain water content was assessed using wet-to-dry ratios (WDR) of brain weight as described previously (Haj-Yasein et al., "Glial-Conditional Deletion of Aquaporin-4 (Aqp4) Reduces Blood-Brain Water Uptake and Confers Barrier Function on Perivascular Astrocyte Endfeet," *Proc. Natl. Acad. Sci. U.S.A.* 108:17815-17820 (2011), which is hereby incorporated by reference in its entirety).

Electrophysiological Recordings—In vivo recordings were obtained from layer II somatosensory cortex. In situ recordings were obtained from layer II in coronal cortical slices prepared from P21-30 mice. ISMs of $K^+$ and $NH4^+$ were pulled from double-barreled pipette glass (PB150-6, WPI) with a tip of 1-3 μm. The pipettes were silanized (coated) with dimethylsilane I (Fluka, Sigma) and filled with either $K^+$ ionophore I cocktail B (Fluka, selectivity coefficient $-1.8 \log(K^+/NH_4^+)$) or NH4+ ionophore I cocktail B (Fluka, $-0.9 \log(NH_4^+/K^+)$). All ISMs were calibrated before and after each experiment (a <5% difference was acceptable) using standard solutions and the calibration data was fitted to the Nikolsky equation to determine electrode slope and interference (Nicholson, C., "Ion-Selective Microelectrodes and Diffusion Measurements as Tools to Explore the Brain Cell Microenvironment," *J. Neurosci. Meth.* 48:199-213 (1993), which is hereby incorporated by reference in its entirety). Whole-cell and gramicidin perforated patch-clamp recordings were performed as described previously (Koyama et al., "GABAergic Excitation After Febrile Seizures Induces Ectopic Granule Cells and Adult Epilepsy," *Nat. Med.* (Epub Jul. 15, 2012); Wang et al., "Taurine Activates Excitatory Non-Synaptic Glycine Receptors on Dopamine Neurones in Ventral Tegmental Area of Young Rats," *J. Physiol.* 1:503-516 (2005), both of which are hereby incorporated by reference in their entirety). Electroencephalogram (EEG) signals were externally filtered at 6 Hz (Filter Butterworth Model by Encore, Axopatch 200B by Axon Instruments), band pass filtered at 1-100 Hz and digitized (Digidata 1440A by Axon Instruments). Ion-sensitive microelectrode (ISM) signals were amplified (FD223a by WPI), externally filtered and digitized as above, and reference field potential traces were subtracted. In selected experiments, wireless electromyogram (EMG) and electroencephalogram (EEG) electrodes were implanted (DSI Physiotel®), and an extracellular microelectrode was placed in the thalamus (ventrobasal complex). Recordings were analyzed offline using pClamp 10.2. Myoclonic events (ME) were defined on the EEG as single or multiple 3-9 Hz polyspike and wave discharges (SWD) of 0.2-2 second duration associated with myoclonic jerks determined by video recording, EMG or direct observation. Whisker stimulation was delivered using a pico spritzer III (Parken Instrumentation) and Master 8 (A.M.P.I.). Stimuli consisted of paired 50 μs air pulses with an inter-stimulus interval of 150 ms, and paired-pulse ratio (PPR) was calculated as previously described (Borgdorff et al., "Facilitating Sensory Responses in Developing Mouse Somatosensory Barrel Cortex," *J. Neurophysiol.* 97:2992-3003 (2007), which is hereby incorporated by reference in its entirety). $NH_4Cl/NH_4Ac$ solutions were pH (7.4) and osmolarity adjusted.

Ion Sensitive Microelectrode (ISM) Fabrication—Ion Sensitive Microelectrodes (ISMs) of $K^+$ and $NH4^+$ were pulled from double-barreled pipette glass (PB150-6, WPI) with a tip of 1-3 μm. The pipettes were silanized (coated) with dimethylsilane I (Fluka, Sigma). The ionophore used for $K^+$ was Fluka 60398 (potassium ionophore I cocktail B), for NH4+ was Fluka 09882 (ammonium ionophore I cocktail B) and for $H^+$/pH was Fluka 95291 (hydrogen ionophore I cocktail A) all obtained from Sigma. The $K^+$ ionophore has a selectivity coefficient relative to $NH_4^+$ of $-1.8 \log(K^+/NH_4^+)$, and the $NH_4^+$ ionophore has a selectivity coefficient relative to $K^+$ of $-0.9 \log(NH_4^+/K^+)$. The backfill solutions for the $K^+$, NH4+, and $H^+$ ISMs were 0.15 M KCl, 0.5 M $NH_4Cl$, and phosphate-buffered saline (PBS) with a pH of 7.4 respectively. The reference barrels were used to record the DC potentials and were filled with 0.15 M NaCl. In selected experiments, single barrel electrodes were also used in combination with single reference electrodes. $K^+$ and $NH_4^+$ ISM traces were subtracted for interference by calculating the mV response to the increase of the other ion in calibration solutions. All ISMs were calibrated before and after each experiment. $K^+$ calibrations were done in 150 mM NaCl that contained doubling steps of $K^+$ over a range of concentrations appropriate for the experiment, usually from 3-48 mM. $NH_4^+$ calibrations were carried out in 150 mM NaCl and aCSF from 0.1-10 mM to determine the sensitivity during the in vivo environment. $H^+$ calibrations were carried out in phosphate buffers from pH 5 to 9, where >90% had a response time of 1-5 seconds and a 51-59 mV response to 1 pH unit change. Calibration data were fitted to the Nikolsky equation to determine electrode slope and interference. Nicholson, C., "Ion-Selective Microelectrodes and Diffusion Measurements as Tools to Explore the Brain Cell Microenvironment," *J. Neurosci. Meth.* 48:199-213 (1993), which is hereby incorporated by reference in its entirety. In all experiments, recordings were used only if the post-experiment calibration did not differ more than 5% from the pre-experiment calibration.

Two-Photon Laser Scanning Microscopy (2PLSM)—A Mai Tai laser (SpectraPhysics) attached to a confocal scanning system (Fluoview 300, Olympus) and an upright microscope (IX51W) was used. Briefly, volume changes and calcium activity were imaged in cortex 100 μm below the pial surface, as described previously, using a 60× (1.1 NA) and a 20× (0.95 NA) lens, respectively. For in vivo volumetry xyzt image series were collected (z-step 1.5 μm, every 5 minutes) with acquisition time<20 seconds and laser power<40 mW. For in vivo calcium imaging, dual channel (rhod-2 and eGFP) frames were collected at 0.2 or 2 Hz. A low sampling rate and <20 mW laser were used to avoid photo damage. Normal calcium signaling was easily abolished if the astrocytes were loaded too long with calcium indicator, the craniotomy diameter was too large and with laser or mechanical injury. Therefore, each animal was tested for optimal loading by performing whisker stimulation, to verify a physiological calcium response. Wang et al., "Astrocytic $Ca^{2+}$ Signalling Evoked by Sensory Stimulation In Vivo," *Nat. Neurosci.* 9:816-823 (2006), which is hereby incorporated by reference in its entirety. A calcium transient was defined as an event where the relative ratio between the rhod-2 and eGFP signal intensities ($\Delta F/F_0$) was >2 standard deviations ($\pi$) from baseline. Beginning and end were defined as $\Delta F/F_0 > 0.5\,\pi$ and $<0.5\,\pi$ respectively. Amplitude was taken as the peak $\Delta F/F_0$ in this interval. For in situ volumentric imaging acute cortical slices were loaded with texas red hydrazide (1.5 μM, a fixable sulforhodamine 101 derivative) in aCSF for 50 minutes. Volume and calcium recordings were analyzed using previously described custom-made software (MatLab Inc.). Thrane et al., "Critical Role of Aquaporin-4 (AQP4) in Astrocytic Ca2+ Signaling Events Elicited by Cerebral Edema," *Proc. Natl. Acad. Sci. U.S.A.* 108:846-851 (2010), which is hereby incorporated by reference in its entirety.

Cell Culture Assays—Cultured neocortical astrocytes were prepared from P1-2 mouse and rat pups as previously described. Wang et al., "Astrocytes Modulate Neural Network Activity by Ca(2)(+)-Dependent Uptake of Extracellular K(+)," *Science Signaling* 5:ra26 (2012); Lin et al., "Gap-Junction-Mediated Propagation and Amplification of Cell Injury," *Nat. Neurosci.* 1:494-500 (1998), which are hereby incorporated by reference in their entirety. For $^{86}$Rb$^+$ experiments the cultures were incubated for 10 minutes±ouabain (1 mM). The potassium analogue $^{86}$Rb$^+$ was then added to each well plate for 15 minutes (1 µCi, Perkin Elmer). The reaction was stopped by placing the cells on ice and washed with ice-cold aCSF. The cells were lysed and $^{86}$Rb$^+$ uptake quantified by liquid scintillation counting (Beckman Coulter). For Na$^+$—K$^+$-ATPase activity, astrocyte cultures were utilized as previously described, and enzyme activity was quantified using the malachite green reaction (Sigma) and analyzed using spectrophotometry. Anupama et al. "Comparison of Na—K ATPase Activity in Rat Brain Synaptosome Under Various Conditions," *Neurochem. Int.* 33:283-286 (1998), which is hereby incorporated by reference in its entirety.

$^1$H-NMR Spectroscopy—Mice were anesthetized using 1.5% isoflurane and decapitated. Forebrains (whole brain minus cerebellum/brainstem) were quickly extracted, frozen in liquid nitrogen, and homogenized in 7.5 mL 12% PCA at 0° C. using a micro-sonicator. The homogenate was centrifuged at 25,000 G for 15 minutes, and the supernatants were neutralized to pH 7.0 with KOH over an ice bath. A further 15 minute centrifugation (25,000 G) separated the resultant KClO$_4$, and the supernatant was lyophilized before being reconstituted with 0.65 ml D$_2$O. $^1$H-NMR spectra were acquired using a 600 mHz Varian Unity NOVA spectrometer equipped with a triple-axis gradient HCN probe (standard room temperature). Signals were acquired following a 90° pulse with a spectral width of 7200 Hz and 32K data points. The time between pulses was 15 seconds and 64 signals were averaged for each spectrum. The sample temperature was 25° C. Integrals of the relevant peaks were converted to µmol/gram wet-weight and normalized NAA (methyl) to increase inter-sample consistency.

In Situ Electrophysiology—Coronal cortical slices were prepared from P21-30 mice, as described previously. Simard et al., "Signaling at the Gliovascular Interface," *J. Neurosci.* 23:9254-9264 (2003); Wang et al., "Taurine Activates Excitatory Non-Synaptic Glycine Receptors on Dopamine Neurones in Ventral Tegmental Area of Young Rats," *J. Physiol.* 1:503-516 (2005), both of which are hereby incorporated by reference in their entirety. All experiments were performed at 32-35° C. NH$_4$Cl/NH$_4$Ac solutions were pH (7.4) and osmolarity adjusted. This age was chosen as in younger pups the GABA reversal potential can be depolarizing (excitatory). Dzhala et al., "NKCC1 Transporter Facilitates Seizures in the Developing Brain," *Nat. Med.* 11:1205-1213 (2005), which is hereby incorporated by reference in its entirety. Whole-cell patch-clamp recordings were done using electrodes with 3-5 M106 resistance, and an intracellular solution containing 135 mM K-methylsulfate, 10 mM KCl, 10 mM hepes, 5 mM NaCl, 2.5 mM Mg-ATP, 0.3 mM Na-GTP (pH 7.3), containing Alexa Fluor® 350 (Invitrogen). Signals were low-pass filtered at 2 kHz and digitized at 10 kHz using Axopatch MultiClamp 700A and Digidata 1320A (Axon Instruments). For volumetric imaging acute cortical slices were loaded with texas red hydrazide (1.5 µM, a fixable sulforhodamine 101 derivative) in aCSF for 50 minutes, and used for volumetric imaging as described previously. Thrane et al., "Critical Role of Aquaporin-4 (AQP4) in Astrocytic Ca2+ Signaling Events Elicited by Cerebral Edema," *Proc. Natl. Acad. Sci. U.S.A.* 108:846-851 (2010), which is hereby incorporated by reference in its entirety.

Immunohistochemistry—Mice were anesthetized and perfused transcardially with 4% paraformaldehyde, and the brains were post-fixed overnight. Serial 16 µm sagittal cryostat sections were cut after overnight cryoprotection in 30% sucrose. Sections were incubated with goat anti-NKCC1 primary antibody (1:200, Sta. Cruz Biotechnology) overnight at 4° C., followed by incubation with an Alexa-488 donkey anti-goat secondary antibody (1:500, Invitrogen). Vectashield containing DAPI (Vector) was used for mounting. Images were taken with a 10× lens in a BX53 Olympus system microscope attached to a DP72 Olympus digital camera.

Statistical Analyses—All analysis was performed using IBM SPSS Statistics 19 and all tests were two-tailed where significance was achieved at α=0.05 level. Where n≥10 for normally distributed data, the unpaired t test or ANOVA were used for independent samples, and paired t test for paired samples. Where n<10 non-parametric tests including Mann-Whitney U and Kruskall-Wallis were used for independent samples, and Wilcoxon signed ranks test for paired samples. Overdose survival was compared using Cox regression model (controlling for the confounding effect of mouse weight).

Figures 5A, 5B, 5C, 5D, 5E, 5F, 5G:
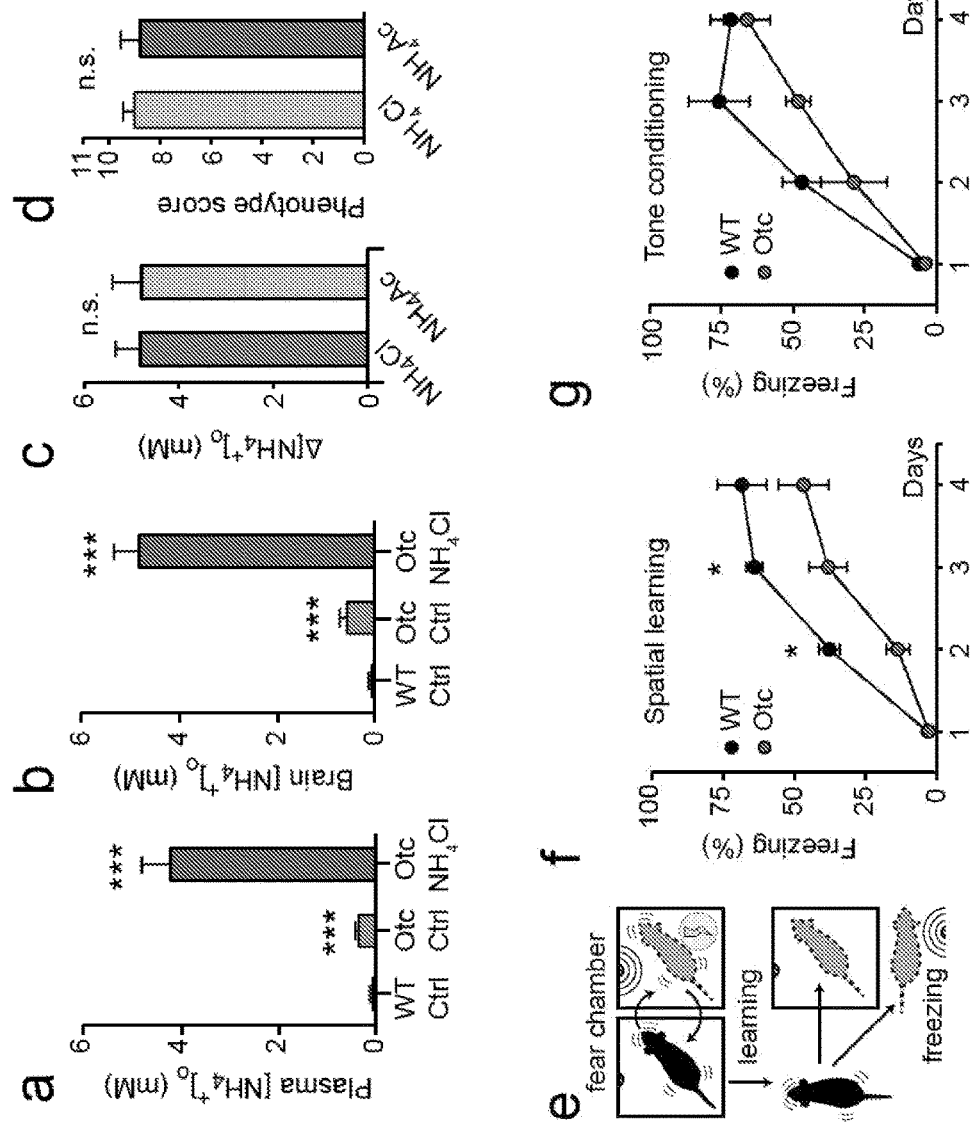
FIGS. 5A-5J illustrate behavioral and biochemical characterization of acute ammonia neurotoxicity.

Example 2—The Otc$^{spf\text{-}ash}$ Mouse Model is Characterized by Acute Ammonia Neurotoxicity To characterize the effects of ammonia on brain function, awake adult male Otc$^{spf\text{-}ash}$ mice were subjected to an acute systemic ammonia load (NH$_4$Cl or NH$_4$Ac, 7.5 mmol kg$^{-1}$ i.p.). This model was associated with a brisk increase in the extracellular ammonia concentration ([NH$_4^+$]$_o$) from 0.32±0.07 to 4.21±0.59 mM in plasma and 0.54±0.18 to 4.83±0.52 mM in brain (FIGS. 5A-5D). Shortly after the injection, the mice developed a stereotypical sequence of neurological impairments, ranging from decreased spontaneous movement to seizures, and in severe cases coma followed by death (FIG. 1A) (Rowe et al., "Natural History of Symptomatic Partial Ornithine Transcarbamylase Deficiency," *New Eng. J. Med.* 314:541-547 (1986), which is hereby incorporated by reference in its entirety). Several behavioral measures were employed to track the progression and severity of ammonia neurotoxicity. Using automated video tracking an early decrease in spontaneous mouse movement was found following the ammonia challenge (13.69±1.48 vs. 0.42±0.22 m min$^{-1}$) (FIG. 1B). A sensory-motor phenotype score was also developed that sensitively detected key aspects of hyperammonemia (0.53±0.28 vs. 9.00±0.46 out of 11) (FIG. 1C) (Ye et al., "Adenovirus-Mediated In Vivo Gene Transfer Rapidly Protects Ornithine Transcarbamylase-Deficient Mice From an Ammonium Challenge," *Pediatr. Res.* 41:527-535 (1997); Guyenet et al., "A Simple Composite Phenotype Scoring System for Evaluating Mouse Models of Cerebellar Ataxia," JoVE (2010), both of which are hereby incorporated by reference in their entirety). Similar to children born with OTC deficiency, the Otc$^{spf\text{-}ash}$ mice displayed neurological dysfunction including impaired learning at baseline (before receiving the ammonia load) (FIGS. 1D, 5E, 5F, 5G) (Cagnon et al., "Hyperammonemia-Induced Toxicity for the Developing Central Nervous System," *Brain Res. Rev.* 56:183-197 (2007); Ye et al., "Adenovirus-Mediated In Vivo Gene Transfer Rapidly Protects Ornithine Transcarbamylase-Deficient Mice From an Ammonium Challenge," *Pediatr. Res.* 41:527-535 (1997); and Ratnakumari et al., "Effects of Congenital Hyperammonemia on the Cerebral and Hepatic Levels of the Intermediates of Energy Metabolism in Spf Mice," *Biochem. Biophys. Res. Comm.* 184:746-751 (1992), all of which are hereby incorporated by reference in their entirety). This likely reflects the baseline excess of [NH$_4^+$]$_o$ in the Otc$^{spf\text{-}ash}$ mice (FIGS. 5A and 5B).

Example 3—Acute Ammonia Exposure Causes a Robust Seizure Phenotype

Figures 1E, 1F, 1G, 1H, 1I:
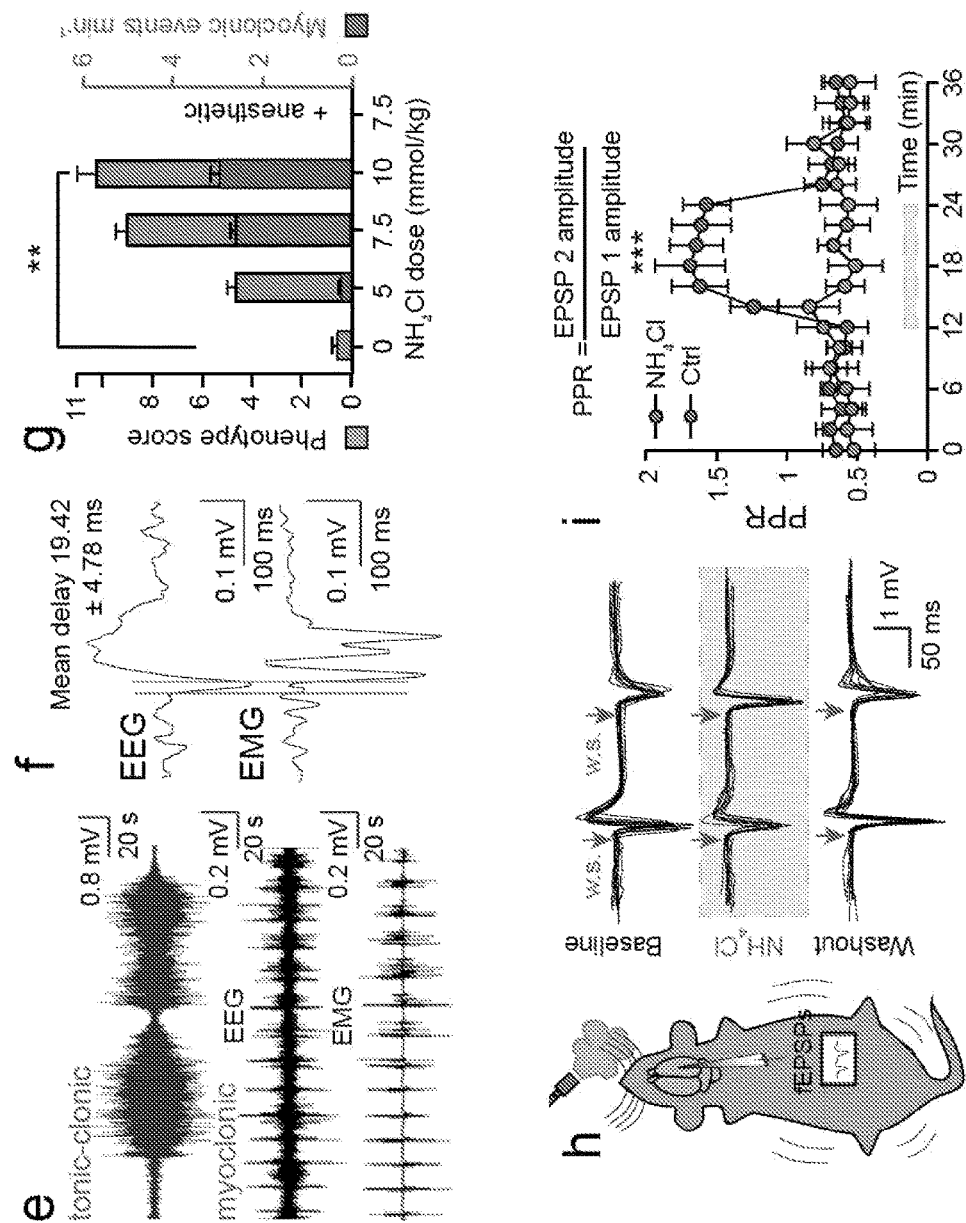

In addition to cognitive, sensory, and motor impairment, children with OTC deficiency typically develop seizures during episodes of hyperammonemia (Cagnon et al., "Hyperammonemia-Induced Toxicity for the Developing Central Nervous System," *Brain Res. Rev.* 56:183-197 (2007); Rowe et al., "Natural History of Symptomatic Partial Ornithine Transcarbamylase Deficiency," *New Eng. J. Med.* 314:541-547 (1986), which are hereby incorporated by reference in their entirety). Around weaning Otc$^{spf-ash}$ mice also developed spontaneous myoclonuses, which are brief (<2 s) involuntary jerky movements thought to be caused by generalized cortical seizure activity (Russell et al., "Familial Cortical Myoclonus With a Mutation in NOL3," *Ann. Neurol.* 72(2):175-83 (2012); DeSalvo et al., "Focal BOLD fMRI Changes in Bicuculline-Induced Tonic-Clonic Seizures in the Rat," *NeuroImage* 50:902-909 (2010), which are hereby incorporated by reference in their entirety). An ammonia challenge was used to precipitate the seizure phenotype and it was found that intermediate doses (7.5 mmol kg$^{-1}$) triggered numerous myoclonic events, whilst a lethal dose (10 mmol kg$^{-1}$) induced longer lasting generalized tonic-clonic seizures (FIG. 1E). Myoclonic events were defined as 3-9 Hz poly-spike and wave electroencephalogram (EEG) discharges, which consistently preceded the electromyogram (EMG) response by 19.42±4.78 seconds (FIG. 1F) (Blumenfeld et al., "Cellular and Network Mechanisms of Spike-Wave Seizures," *Epilepsia* 46:21-33 (2005); Hamer et al., "Electrophysiology of Focal Clonic Seizures in Humans: A Study Using Subdural and Depth Electrodes," *Brain* 126: 547-555 (2003), which are hereby incorporated by reference in their entirety). It was found that the frequency of myoclonic events closely correlated with overall disease severity (FIG. 1G). Importantly, both overall phenotype and myoclonic events were entirely masked by anesthesia, emphasizing the need for recordings in awake animals.

Example 4—Cortical Ammonia Toxicity Causes Disinhibition of Neuronal Firing

Figures 5H, 5I, 5J:
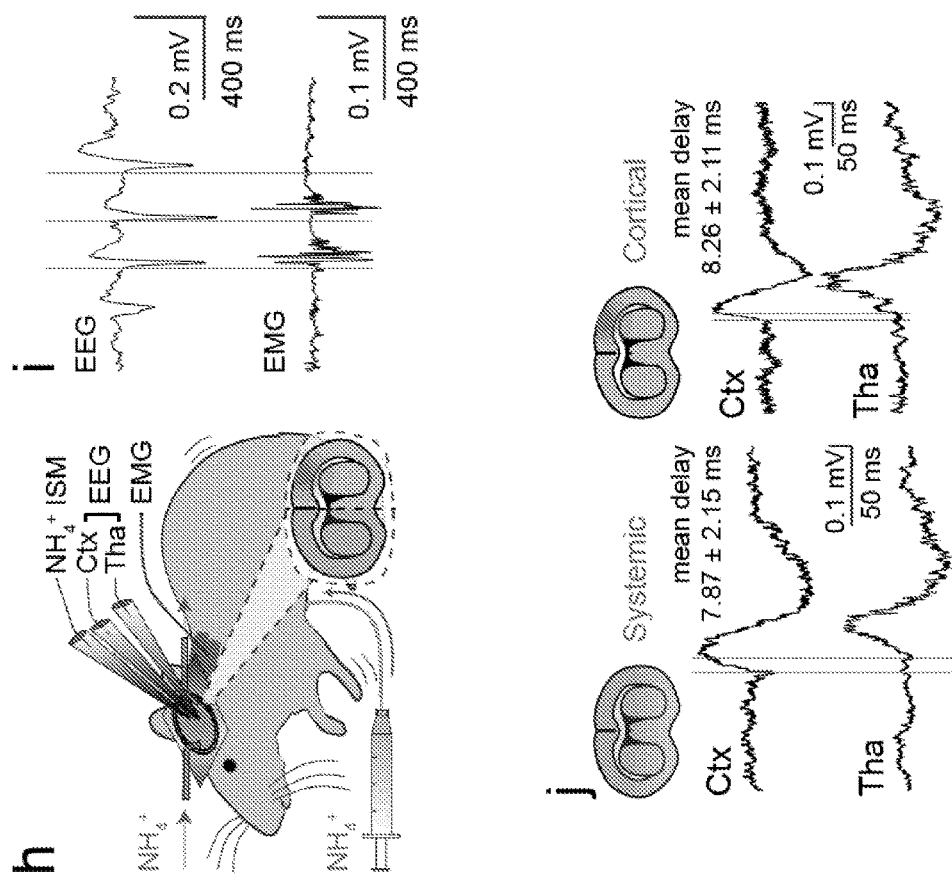

To explore whether cortical ammonia toxicity alone is sufficient to generate neurological dysfunction, ammonia was applied directly on the cortex of awake mice. Cortical application of 10 mM NH$_4$Cl caused a 5.82±0.18 mM increase in [NH$_4^+$]$_o$ and reproduced the seizure phenotype of systemic ammonia toxicity (FIGS. 5H, 5J and Table 1, infra). In Table 1, NH$_4^+$ and K$^+$ ISMS recordings from cortex of awake Otc$^{spf-ash}$ mice are shown. Data are shown as mean±SEM.

TABLE 1

| Bumetanide Treatment Does Not Affect Cortical Ammonia or Potassium Concentrations | | | | | | |
|---|---|---|---|---|---|---|
| | [NH$_4^+$]$_o$ (mM) | n (animals) | P value Mann-Whitney U test | Δ[K$^+$]$_o$ (mM) | n (animals) | P value Mann-Whitney U test |
| CORTICAL SUPERFUSION | | | | | | |
| Control | 0.45 ± 0.17 | 6 | | 0.0058 ± 0.019 | 6 | |
| BUM | 0.52 ± 0.11 | 6 | 0.59 | 0.0025 ± 0.018 | 6 | 0.94 |
| NH$_4$Cl | 5.82 ± 0.18 | 6 | | 2.24 ± 0.17 | 10 | |
| NH$_4$Cl + BUM | 5.78 ± 0.13 | 6 | 0.87 | 2.17 ± 0.12 | 9 | 0.66 |
| INTRAPERITONEAL INJECTION | | | | | | |
| Control | 0.48 ± 0.12 | 6 | | 0.015 ± 0.025 | 9 | |
| BUM | 0.42 ± 0.16 | 6 | 0.39 | 0.0073 ± 0.015 | 6 | 0.53 |
| NH$_4$Cl | 4.83 ± 0.52 | 7 | | 1.93 ± 0.19 | 10 | |
| NH$_4$Cl + BUM | 4.70 ± 0.32 | 6 | 0.83 | 1.97 ± 0.17 | 6 | 0.92 |

Additionally, cortical myoclonic discharges preceded those in the thalamus by 7.87±2.15 ms (systemic) and 8.26±2.11 ms (cortical) (FIG. 5J) (DeSalvo et al., "Focal BOLD fMRI Changes in Bicuculline-Induced Tonic-Clonic Seizures in the Rat," *NeuroImage* 50:902-909 (2010), which is hereby incorporated by reference in its entirety).

Next, it was investigated how cortical ammonia toxicity leads to neurological dysfunction and seizures. Previous studies using reduced preparations have indicated that ammonia can impair inhibitory neurotransmission (Lux, H. D., "Ammonium and Chloride Extrusion: Hyperpolarizing Synaptic Inhibition in Spinal Motor Neurons," *Science* 173:555-557 (1971); Raabe, W. A., "Ammonia and Disinhibition in Cat Motor Cortex by Ammonium Acetate, Monofluoroacetate and Insulin-Induced Hypoglycemia," *Brain. Res.* 210:311-322 (1981); Irie et al., "Chloride Concentration in Cultured Hippocampal Neurons Increases During Long-Term Exposure to Ammonia Through Enhanced Expression of an Anion Exchanger," *Brain Research* 806: 246-256 (1998); Szerb et al., "Effect of Ammonium Ions on Synaptic Transmission in the Mammalian Central Nervous System," *Prog. Neurobiol.* 39:135-153 (1992), all of which are hereby incorporated by reference in their entirety). These observations were expanded using the awake mouse model presented herein, and therefore paired-pulse whisker stimulation was employed as a measure of cortical inhibitory function. Borgdorff et al., "Facilitating Sensory Responses in Developing Mouse Somatosensory Barrel Cortex," *J. Neurophysiol.* 97:2992-3003 (2007), which is hereby incorporated by reference in its entirety. The whisker stimulation paradigm elicits two successive field excitatory post-synaptic potentials (fEPSP), where the second fEPSP has lower amplitude due to activation of cortical inhibitory networks (quantified by a paired-pulse ratio (PPR)<1). It was found that cortical ammonia application impaired cortical inhibition, illustrated by an increased PPR from 0.64±0.13 (control) to 1.56±0.24 (ammonia), which recovered to 0.61±0.15 (washout) (FIGS. 1H, 1I). Taken together, using in vivo methods a direct link between seizure generation and cortical disinhibition during ammonia toxicity was demonstrated.

Example 5—Ammonia-Induced [K$^+$]$_o$ Increase Causes Neurological Dysfunction

Figures 2A, 2B, 2C, 2D:
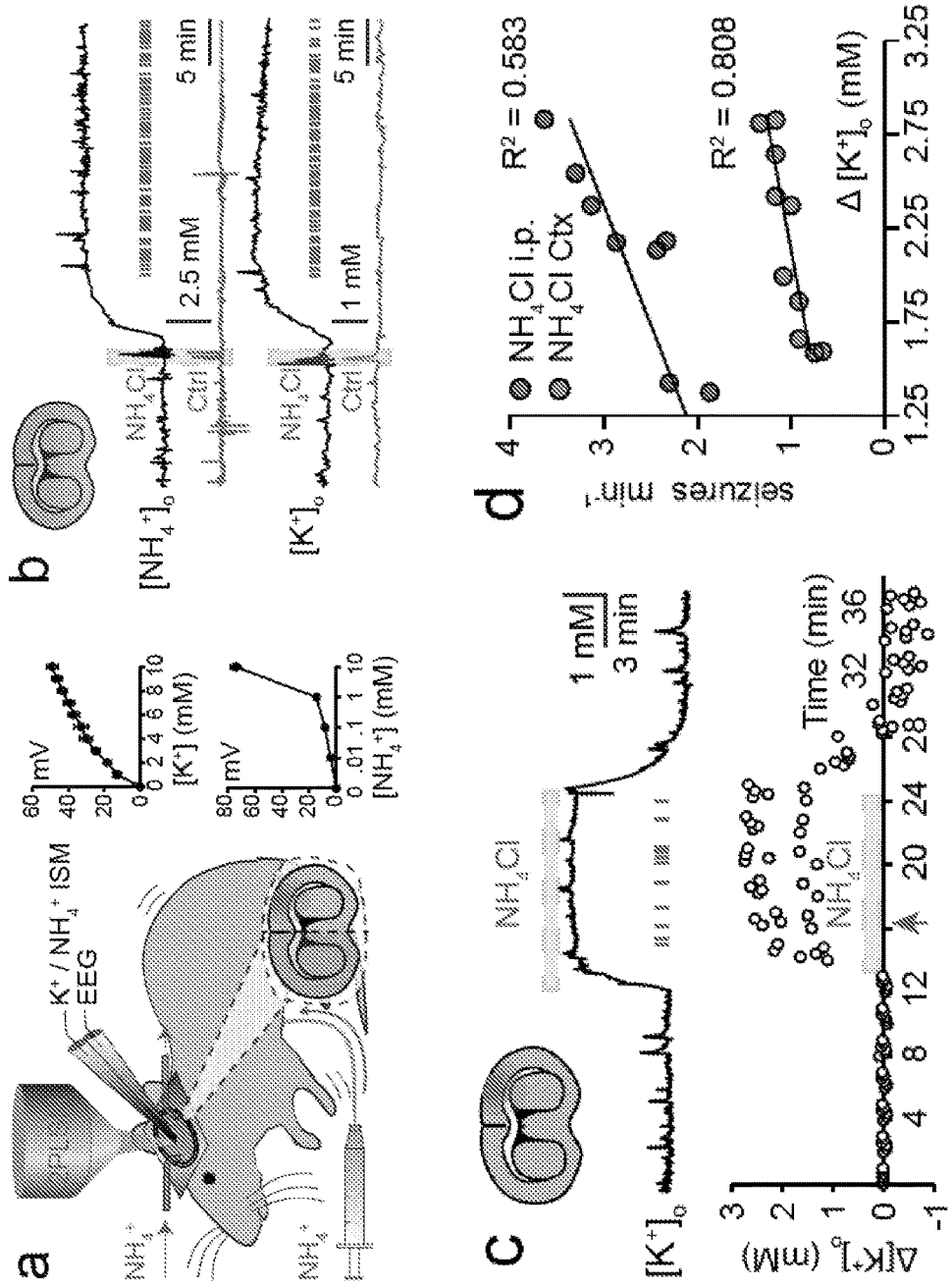
Figures 6A, 6B, 6C, 6D, 6E, 6F:
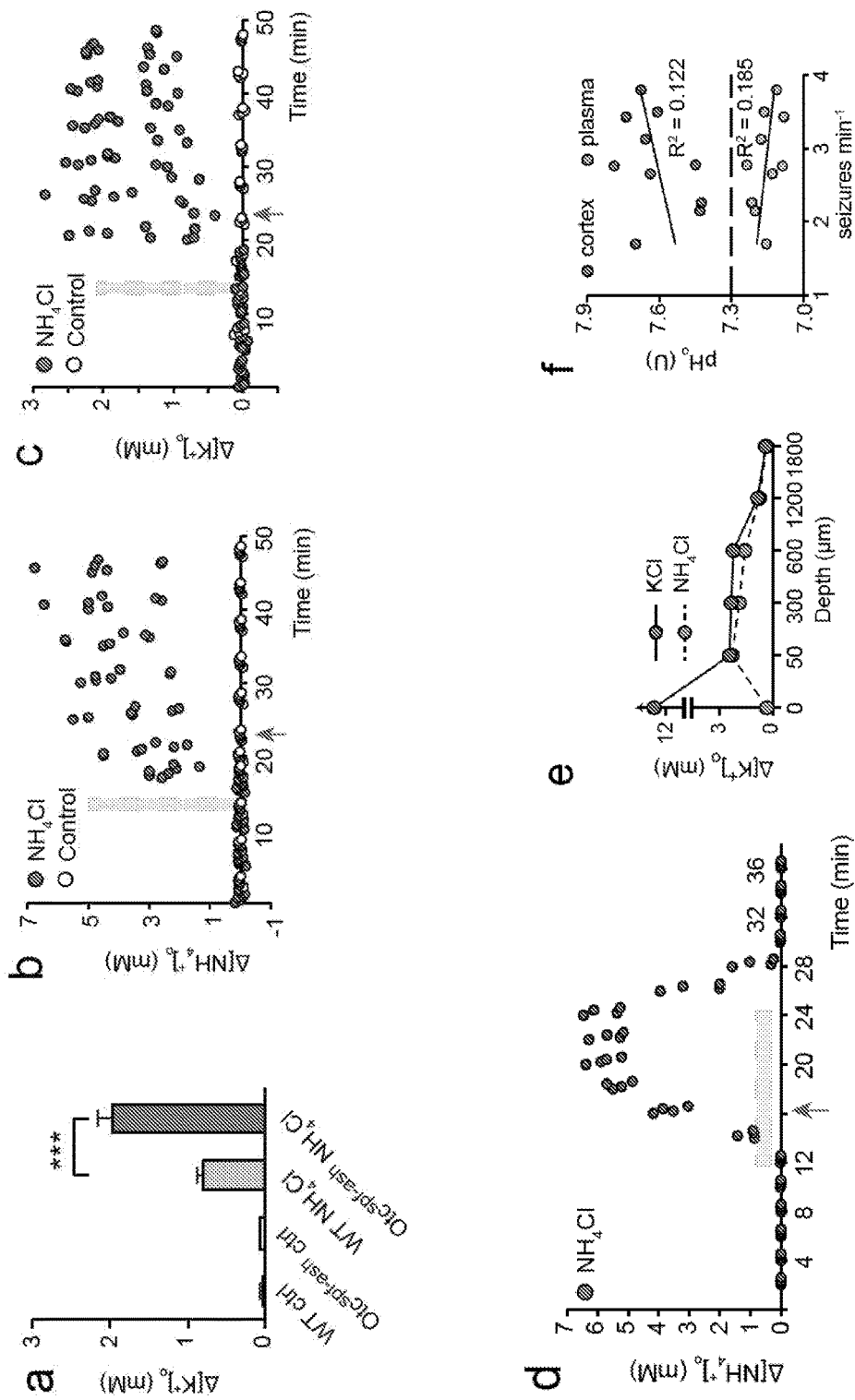
FIGS. 6A-6F illustrate that ammonia neurotoxicity is associated with increased cortical [NH$_4^+$]$_o$ and [K$^+$]$_o$ increase.

Potassium homeostasis is primarily regulated by astrocytes and closely linked to inhibitory neurotransmission. Dzhala et al., "NKCC1 Transporter Facilitates Seizures in the Developing Brain," *Nat. Med.* 11:1205-1213 (2005); Amiry-Moghaddam et al., "Delayed K$^+$ Clearance Associated With Aquaporin-4 Mislocalization: Phenotypic Defects in Brains of Alpha-Syntrophin-Null Mice," *Proc. Nat. Acad. Sci. U.S.A.* 100:13615-13620 (2003); Wang et al., "Astrocytic Ca$^{2+}$ Signalling Evoked by Sensory Stimulation In Vivo," *Nat. Neurosci.* 9:816-823 (2006); Sofroniew, M. V., "Molecular Dissection of Reactive Astrogliosis and Glial Scar Formation," *Trends Neurosci.* 32:638-647 (2009); Chen et al., "Spatial Buffering of Potassium Ions in Brain Extracellular Space," *Biophysical Journal* 78:2776-2797 (2000), all of which are hereby incorporated by reference in their entirety. Previous studies have indicated that ammonia can compromise astrocyte potassium buffering in culture and slice via several mechanisms. Alger et al., "Ammonia Does Not Selectively Block IPSPs in Rat Hippocampal Pyramidal Cells," *J. Neurophysiol.* 49:1381-1391 (1983); Stephan et al., "Kir4.1 Channels Mediate a Depolarization of Hippocampal Astrocytes Under Hyperammonemic Conditions In Situ," *Glia* 60:965-978 (2012); Allert et al., "Ammonia-Induced Depolarization of Cultured Rat Cortical Astrocytes," *Brain Res.* 782:261-270 (1998), which are hereby incorporated by reference in their entirety. Therefore, the effects of ammonia on cortical [K$^+$]$_o$ in awake mice were explored using NH$_4^+$ and K$^+$ ion-sensitive microelectrodes (ISM). Nicholson, C., "Ion-Selective Microelectrodes and Diffusion Measurements as Tools to Explore the Brain Cell Microenvironment," *J. Neurosci. Methods* 48:199-213 (1993), which is hereby incorporated by reference in its entirety. Both systemically (7.5 mmol kg$^{-1}$) and cortically (10 mM) applied ammonia increased [K$^+$]$_o$ by 1.93±0.19 mM and 2.24±0.17 mM, respectively, from a resting level of 3.91±0.27 mM (subtracted for NH$_4^+$ interference) (FIGS. 2A-2C, 6A). Following washout of ammonia, [K$^+$]$_o$ recovered to a level slightly below baseline as the neurological manifestations subsided (FIG. 2C). The [K$^+$]$_o$ increase recorded consistently preceded and strongly correlated with myoclonic events (systemic 4.91±0.35 minutes and cortical 2.88±0.20 minutes) (FIGS. 2B-2D, 6B-6E). Conversely, the pH effects of ammonia were mild, delayed and correlated poorly with clinical phenotype (FIG. 6F). Chesler, M., "Regulation and Modulation of pH in the Brain," *Physiol. Rev.* 83:1183-1221 (2003), which is hereby incorporated by reference in its entirety.

Figures 2E, 2F, 2G, 2H, 2I:
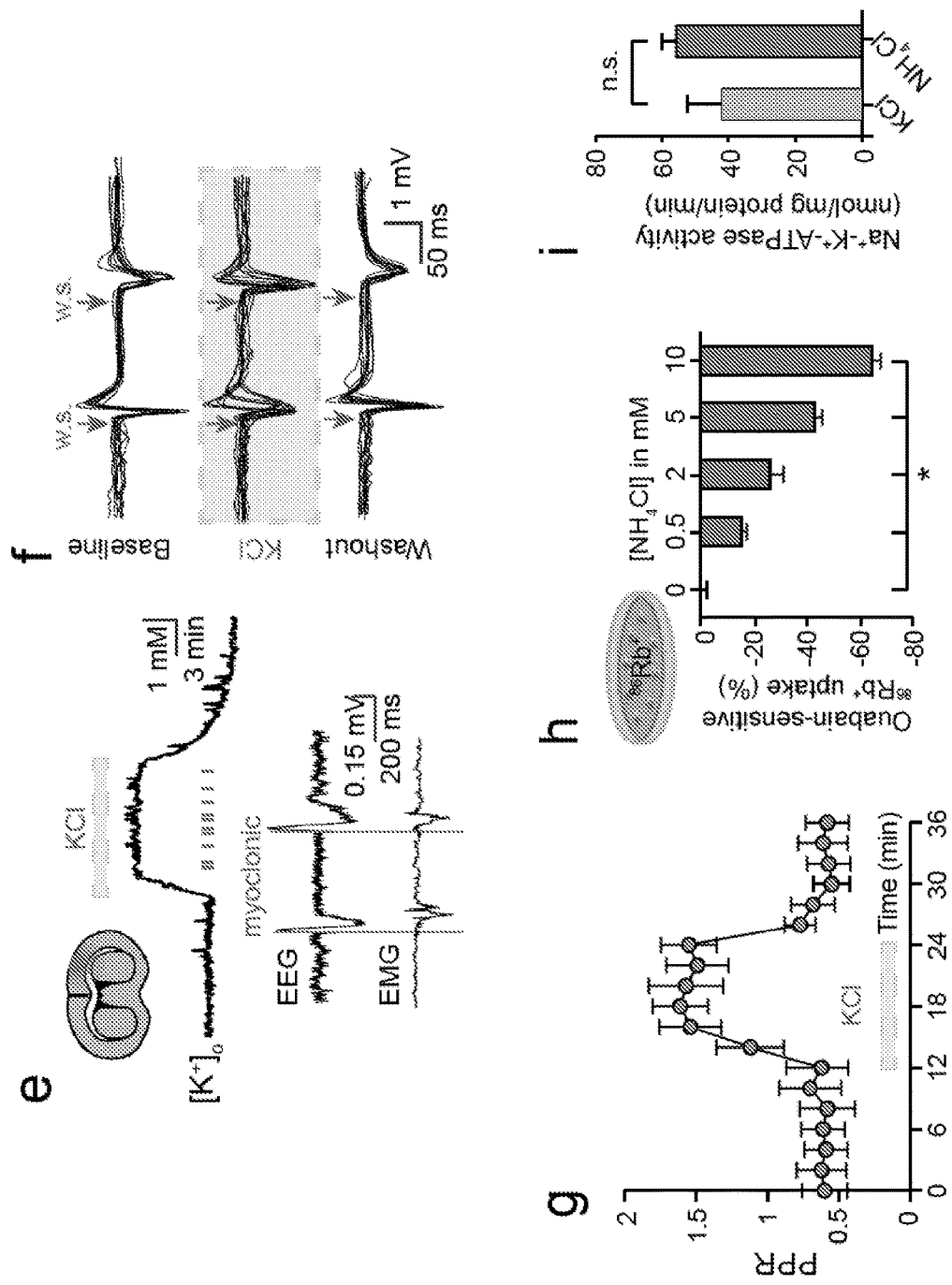

To determine whether the ammonia induced increase in cortical [K$^+$]$_o$ alone is sufficient to cause neurological dysfunction, KCl (12.5 mM) was superfused across the cortex of awake mice increasing [K$^+$]$_o$ by 2.37±0.03 mM. Strikingly, this caused the mice to develop myoclonic events similar to those seen in ammonia neurotoxicity (FIG. 2E). Using the paired-pulse paradigm outlined above, it was demonstrated that KCl induced seizures were associated with cortical disinhibition, illustrated by a PPR of 1.48±0.22 that recovered to 0.63±0.14 after washout (FIG. 2F, 2G). For the first time in vivo, it was shown that ammonia induced [K$^+$]$_o$ increase is sufficient to generate neuronal disinhibition and seizures.

Example 6—Ammonia Competes with Potassium for Uptake in Astrocytes

Figures 3A, 3B, 3C:
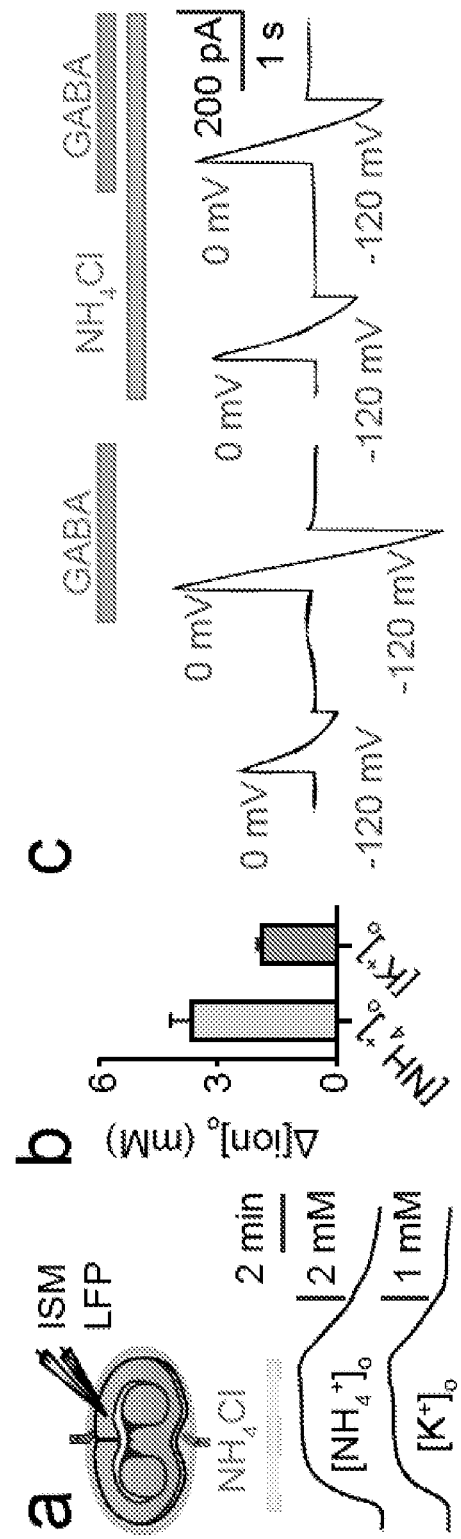
FIGS. 3A-3J illustrate that excess ammonia and potassium cause a depolarization of the neuronal GABA reversal potential ($E_{GABA}$).

More than 4-times as much NH$_4^+$ crosses astrocyte membranes for detoxification by glutamine synthetase than any other cell type in the brain (FIGS. 3A, 3B). Cooper et al., "The Metabolic Fate of 13N-Labeled Ammonia in Rat Brain," *J. Biol. Chem.* 254:4982-4992 (1979), which is hereby incorporated by reference in its entirety. It was found that this enzymatic trapping restricted ammonia diffusion to the cortex and inhibiting glutamine synthetase with L-methionine sulfoximine (MSO) worsened [NH$_4^+$]$_o$ increase and neurological phenotype (FIGS. 7A-7F).

Figures 7A, 7B, 7C, 7D:
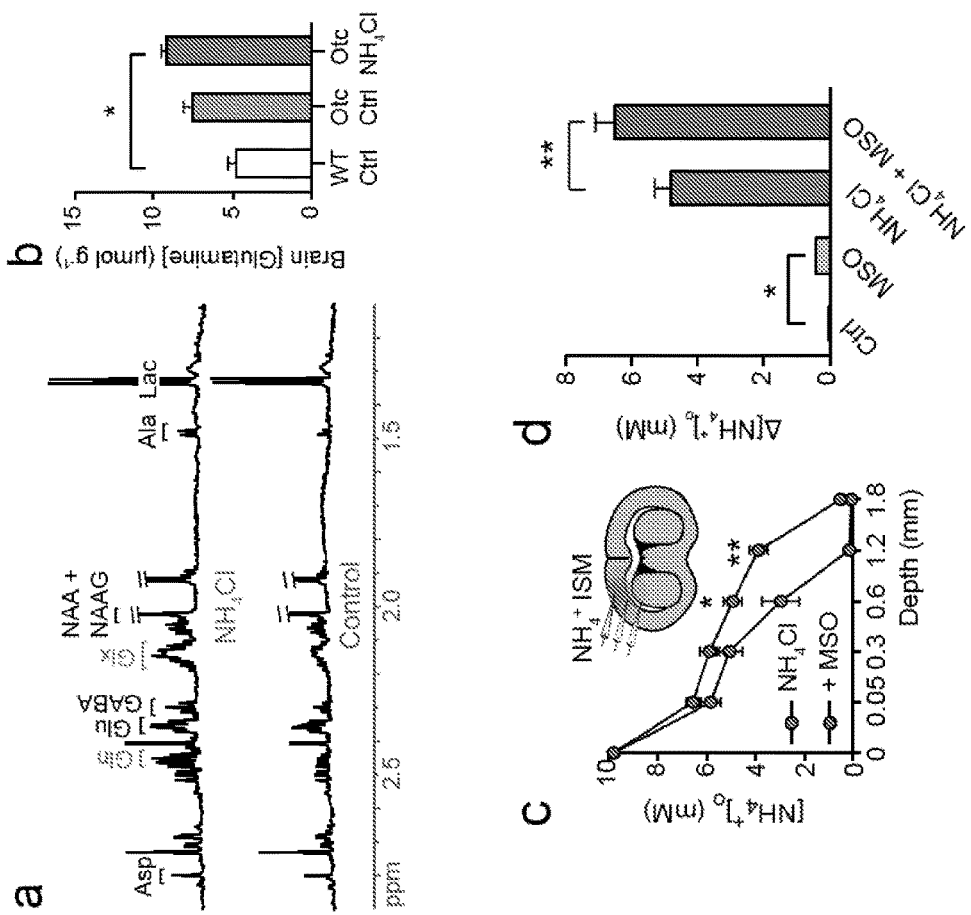
FIGS. 7A-7G depict enzymatic sequestration of ammonia in astrocytes.
Figures 7E, 7F, 7G:
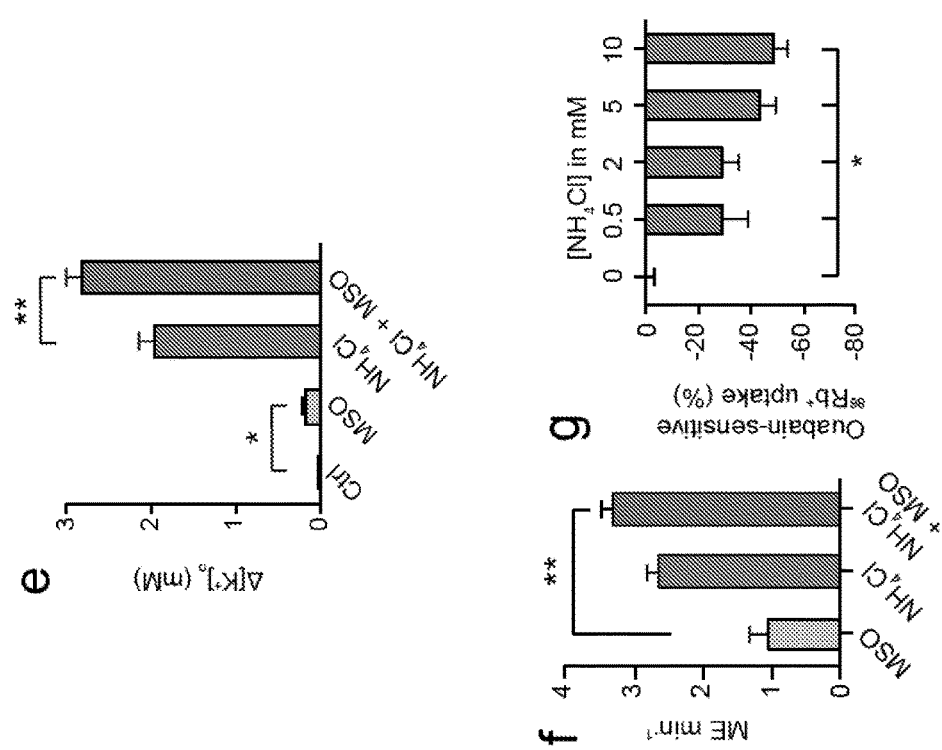
Figures 8A, 8B, 8C, 8D, 8E:
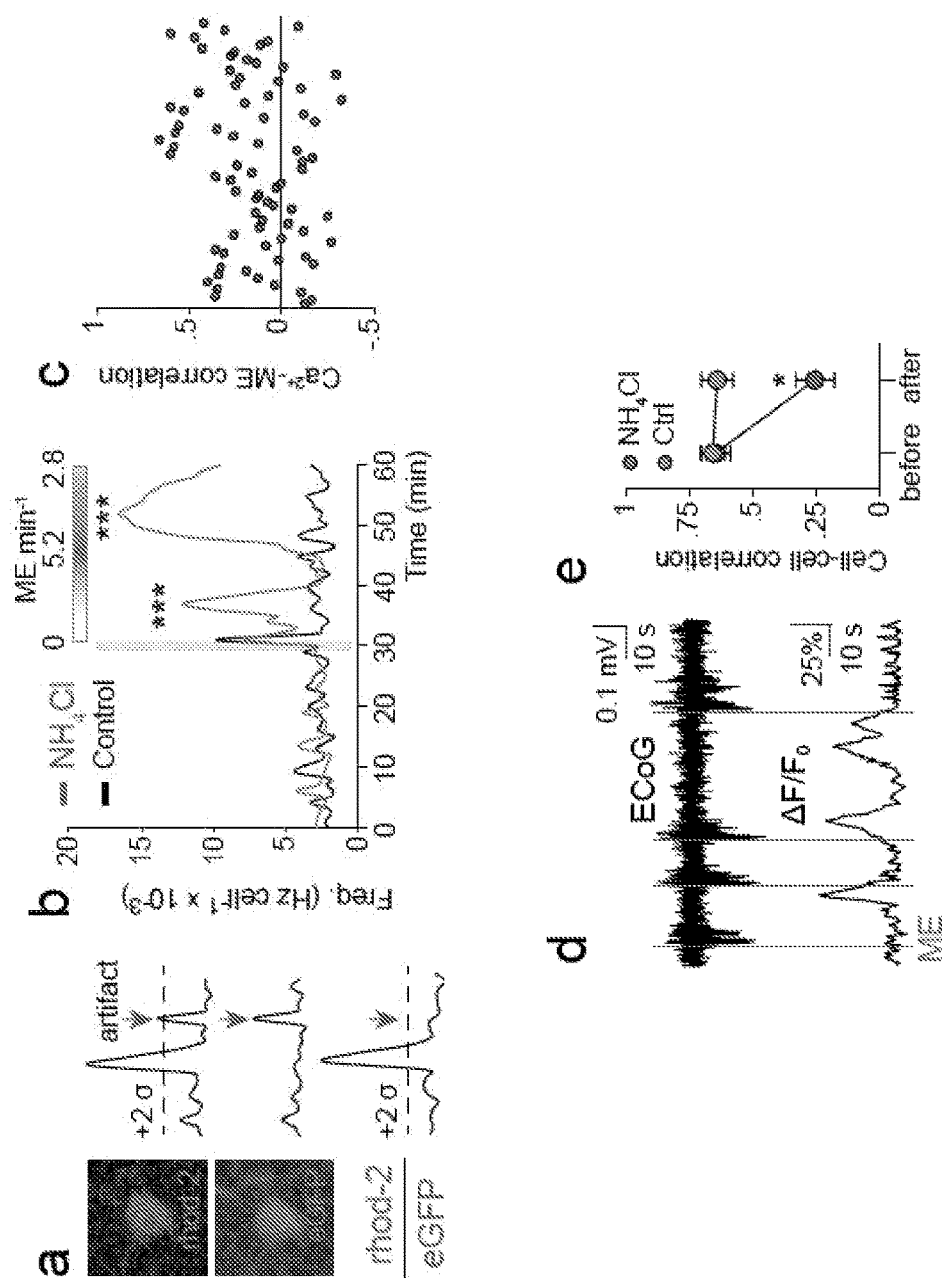
FIGS. 8A-8K show ammonia effects on astrocyte calcium signaling and volume regulation.
Figures 8F, 8G, 8H, 8I:
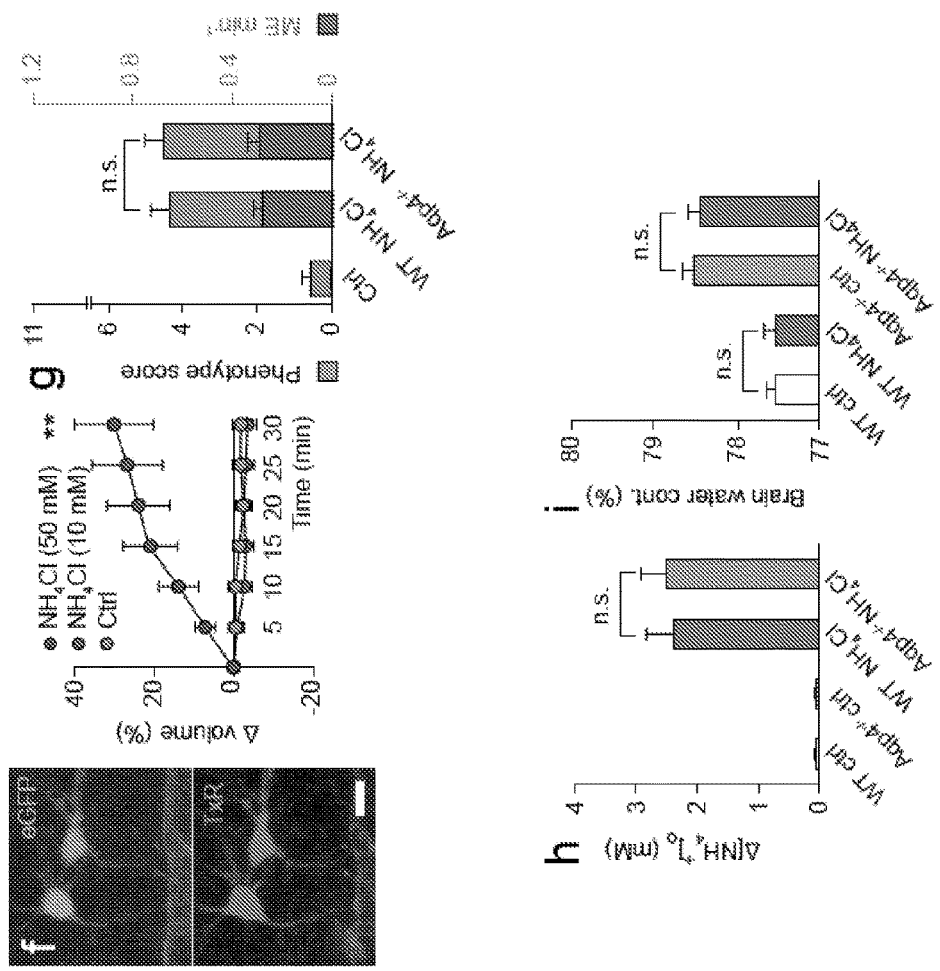
Figures 8J, 8K:
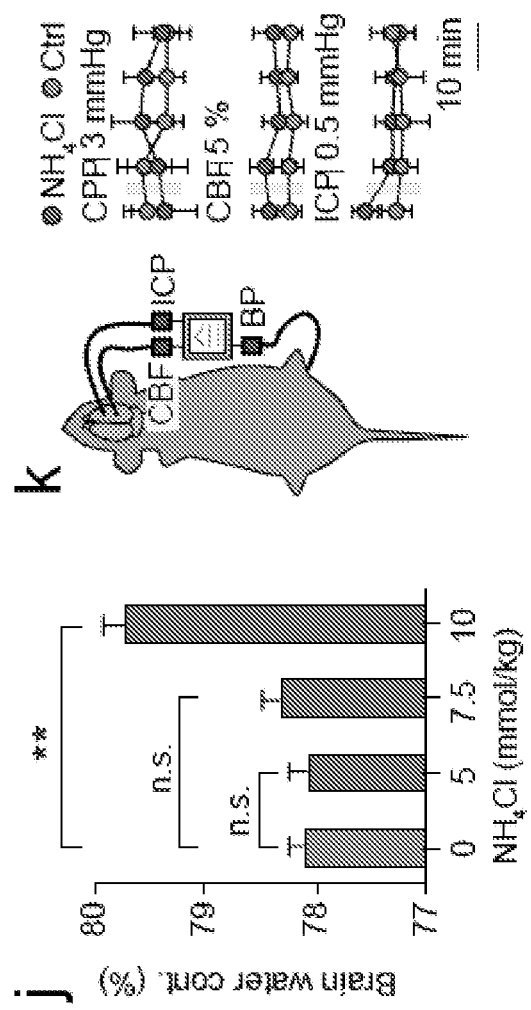

It was hypothesized that an excess NH$_4^+$ load on astrocyte membranes could lead to decreased K$^+$ buffering by either indirectly impairing (pump failure) or directly competing (pump overactivity) for uptake. The gradients driving astrocyte uptake of potassium are largely dependent on Na$^+$—K$^+$-ATPase (NKA) activity. Wang et al., "Astrocytes Modulate Neural Network Activity by Ca(2)(+)-Dependent Uptake of Extracellular K(+)," *Science Sig.* 5:ra26 (2012); Kirischuk et al., "Sodium Dynamics: Another Key to Astroglial Excitability?," *Trends Neurosci.* 35:497-506 (2012); Xiong et al., "Sodium Pump Activity, Not Glial Spatial Buffering, Clears Potassium After Epileptiform Activity Induced in the Dentate Gyms," *J. Neurophys.* 83:1443-1451 (2000), all of which are hereby incorporated by reference in their entirety. Using biologically relevant concentrations of ammonia (0.5-10 mM), a dose-dependent reduction was demonstrated in NKA-dependent (ouabain-sensitive) potassium analogue rubidium ($^{86}$Rb$^+$) uptake in cultured astrocytes (FIG. 2H). In contrast, neuronal $^{86}$Rb$^+$ uptake was more inconsistently reduced, compatible with the hypothesis that neurons play a less prominent role in potassium buffering (FIG. 7G). Wang et al., "Astrocytes Modulate Neural Network Activity by Ca(2)(+)-Dependent Uptake of Extracellular K(+)," *Science Sig.* 5:ra26 (2012), which is hereby incorporated by reference in its entirety. NH$_4$Cl was then substituted for KCl in a cell-free NKA assay, and it found that NH$_4$Cl alone was able to maintain normal NKA activity (FIG. 2I). These observations are further supported by previous studies of renal NKA. Wall et al., "NH4$^+$ Transport Mediated by Na($^+$)—K($^+$)-ATPase in Rat Inner Medullary Collecting Duct," *Am. J. Physiol.* 267:F660-670 (1994); Kurtz et al., "Ammonium As a Substrate for Na$^+$—K$^+$-ATPase in Rabbit Proximal Tubules," *Am. J. Physiol.* 250: F497-502 (1986), both of which are hereby incorporated by reference in their entirety. Notably, NH$_4^+$ and K$^+$ ions have a comparable hydrated radius and charge, and can permeate potassium channels with similar efficacy. Marcaggi et al., "Neuron-Glial Trafficking of NH4$^+$ and K$^+$: Separate Routes of Uptake Into Glial Cells of Bee Retina," *Eur. J. Neurosci.* 19(4):966-976 (2004); Stephan et al., "Kir4.1 Channels Mediate a Depolarization of Hippocampal Astrocytes Under Hyperammonemic Conditions In Situ," *Glia* 60:965-978 (2012), both of which are hereby incorporated by reference in their entirety. These results explain the increased NKA activity previously observed during ammonia toxicity due to an increase in overall substrate ([NH4$^+$]$_o$ and [K$^+$]$_o$). Ratnakumari et al., "Na$^+$,K($^+$)-ATPase Activites are Increased in Brain in Both Congenital and Acquired Hyperammonemic Syndromes," *Neurosci. Lett.* 197:89-92 (1995), which is hereby incorporated by reference in its entirety. Combined, these observations indicate that ammonia competitively inhibits NKA mediated potassium buffering in astrocytes, causing the sustained increase in [K$^+$]$_o$ observed in vivo.

Example 7—Ammonia Triggers Increased Astrocyte Calcium Signaling But Not Swelling During increased neuronal firing, rapid [K$^+$]$_o$ clearance via NKA is partly dependent on astrocyte calcium signaling in response to neurotransmitter release. Wang et al., "Astrocytes Modulate Neural Network Activity by Ca($^2$)($^+$)-Dependent Uptake of Extracellular KC)," *Science Sig.* 5:ra26 (2012); Koizumi et al., "Dynamic Inhibition Off Excitatory Synaptic Transmission by Astrocyte-Derived ATP in Hippocampal Cultures," *Proc. Natl. Acad. Sci. U.S.A.* 100: 11023-11028 (2003); Gourine et al., "Astrocytes Control Breathing Through PH-Dependent Release of ATP," *Science* 329:571-575 (2010), which are hereby incorporated by reference in their entirety. Using two-photon laser scanning microscopy (2PLSM) in awake Otc$^{spf-ash}$ mice, it was shown that ammonia neurotoxicity is associated with increased calcium signaling (transient frequency 2.67±0.36 to 9.03±1.16 Hz cell$^{-1}$ 10$^{-3}$). Thrane et al., "Real-Time Analysis of Microglial Activation and Motility in Hepatic and Hyperammonemic Encephalopathy," *Neuroscience* 220: 247-55 (2012), which is hereby incorporated by reference in its entirety. The increased astrocyte signaling preceded the onset of myoclonic events by 1.58±0.37 minutes, similar to the [K$^+$]$_o$ increase (FIG. 2J, Table 2, infra).

TABLE 2

Astrocyte Calcium Signaling During Acute Ammonia Neurotoxicity in Awake Mice.

|  | Ctrl (n = 62) | NH$_4$Cl (n = 52) |
| --- | --- | --- |
| Freq. (Hz cell$^{-1}$ × 10$^{-3)}$) | 2.67 ± 0.36 | 9.03 ± 1.16 |
| Amplitude (ΔF/F$_0$) | 0.48 ± 0.11 | 0.47 ± 0.32 |
| Duration (s) | 18.98 ± 3.05 | 21.51 ± 4.55 |
| Cell-cell correlation | 0.65 ± 0.06 | 0.26 ± 0.08 |

Data in Table 2 is from analysis of 2PLSM xyt series, where calcium indicator rhod-2 was used to detect astrocyte calcium transients 100 μm below the pial surface. Data are shown as mean±SEM.

These observations may represent a compensatory increase in NKA to cope with the excess [NH4$^+$]$_o$ and [K$^+$]$_o$ load (Ratnakumari et al., "Na+,K(+)-ATPase Activites are Increased in Brain in Both Congenital and Acquired Hyperammonemic Syndromes," *Neurosci. Lett.* 197:89-92 (1995), which is hereby incorporated by reference in its entirety). It was also found that ammonia desynchronized astrocyte calcium transients (r shift 0.65±0.06 to 0.26±0.08), which could represent a breakdown neuron-to-glia communication in ammonia neurotoxicity (FIGS. 8A-8E). Thrane et al., "Real-Time Analysis of Microglial Activation and Motility in Hepatic and Hyperammonemic Encephalopathy," *Neuroscience* 220:247-55 (2012); Wang et al., "Astrocytic Ca$^{2+}$ Signalling Evoked by Sensory Stimulation In Vivo," *Nat. Neurosci.* 9:816-823 (2006), both of which are hereby incorporated by reference in their entirety.

An extensive ex vivo literature indicates that ammonia-induced astrocyte dysfunction due to swelling and brain edema is critical for ammonia neurotoxicity (Butterworth, R. F., "Pathophysiology of Hepatic Encephalopathy: A New Look at Ammonia," *Metab. Brain Dis.* 17:221-227 (2002); Jayakumar et al., "Glutamine in the Mechanism of Ammonia-Induced Swelling," *Neurochem. Int.* 48:623-628 (2006); Rama Rao et al., "Brain Aquaporin-4 in Experimental Acute Liver Failure," *J. Neuropath. Experi. Neuro.* 69:869-879 (2010); Zielinska et al., "Excitotoxic Mechanism of Cell Swelling in Rat Cerebral Cortical Slices Treated Acutely With Ammonia," *Neurochem. Int.* 43:299-303 (2003), all of which are hereby incorporated by reference in their entirety). Using 2PLSM in awake Otc$^{spf-ash}$ mice to image eGFP expressed in astrocytes under the Glt1 promoter it was found that ammonia caused no significant astrocyte swelling (FIG. 2K). Thrane et al., "Critical Role of Aquaporin-4 (AQP4) in Astrocytic Ca2+ Signaling Events Elicited by Cerebral Edema," *Proc. Natl. Acad. Sci. U.S.A.* 108:846-851 (2010), which is hereby incorporated by reference in its entirety. Instead, a transient shrinkage of 5.04±0.85% was found that could reflect increased NKA activity. Ratnakumari et al., "Na$^+$,K($^+$)-ATPase Activites are Increased in Brain in Both Congenital and Acquired Hyperammonemic Syndromes," *Neurosci. Lett.* 197:89-92 (1995); Thrane et al., "Critical Role of Aquaporin-4 (AQP4) in Astrocytic Ca2+ Signaling Events Elicited by Cerebral Edema," *Proc. Natl. Acad. Sci. U.S.A.* 108:846-851 (2010), both which are hereby incorporated by reference in their entirety. Additionally, deletion of astrocyte water channel aquaporin-4 (AQP4) did not improve neurological dysfunction. Thrane et al., "Critical Role of Aquaporin-4 (AQP4) in Astrocytic Ca2+ Signaling Events Elicited by Cerebral Edema," *Proc. Natl. Acad. Sci. U.S.A.* 108:846-851 (2010); Lichter-Konecki et al., "Gene Expression Profiling of Astrocytes From Hyperammonemic Mice Reveals Altered Pathways for Water and Potassium Homeostasis In Vivo," *Glia* 56:365-377 (2008), both of which are hereby incorporated by reference in their entirety. Astrocyte swelling or brain edema were only elicited in terminal stages of ammonia neurotoxicity (FIGS. 8F-8K). Rangroo Thrane et al., "Real-Time Analysis of Microglial Activation and Motility in Hepatic and Hyperammonemic Encephalopathy," *Neuroscience* 220:247-255 (2012), which is hereby incorporated by reference in its entirety. Taken together, it is shown here that ammonia neurotoxicity is characterized by a failure of astrocyte potassium but not volume homeostasis (FIG. 2L).

Example 8—Ammonia Depolarizes E$_{GABA}$ in Cortical Neurons Via NKCC1

To explore the link between impaired astrocyte potassium buffering and neuronal disinhibition, next pyramidal neurons were patched in acute cortical slices perfused with ammonia. Adding 7 mM ammonia to the perfusate reproduced the increase in [NH$_4$$^+$]$_o$ and [K$^+$]$_o$ observed in vivo (3.67±0.53 mM and 1.88±0.13 mM respectively) (FIGS. 3A, 3B).

Figures 9A, 9B:
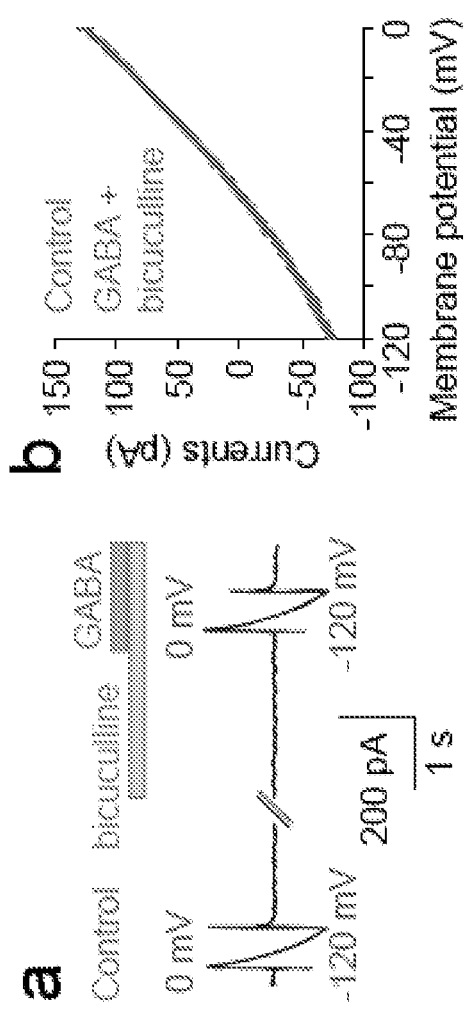
FIGS. 9A-9B show GABA-currents recorded during ramp voltage are entirely $GABA_A$-receptor dependent.
Figures 10A, 10B, 10C, 10D:
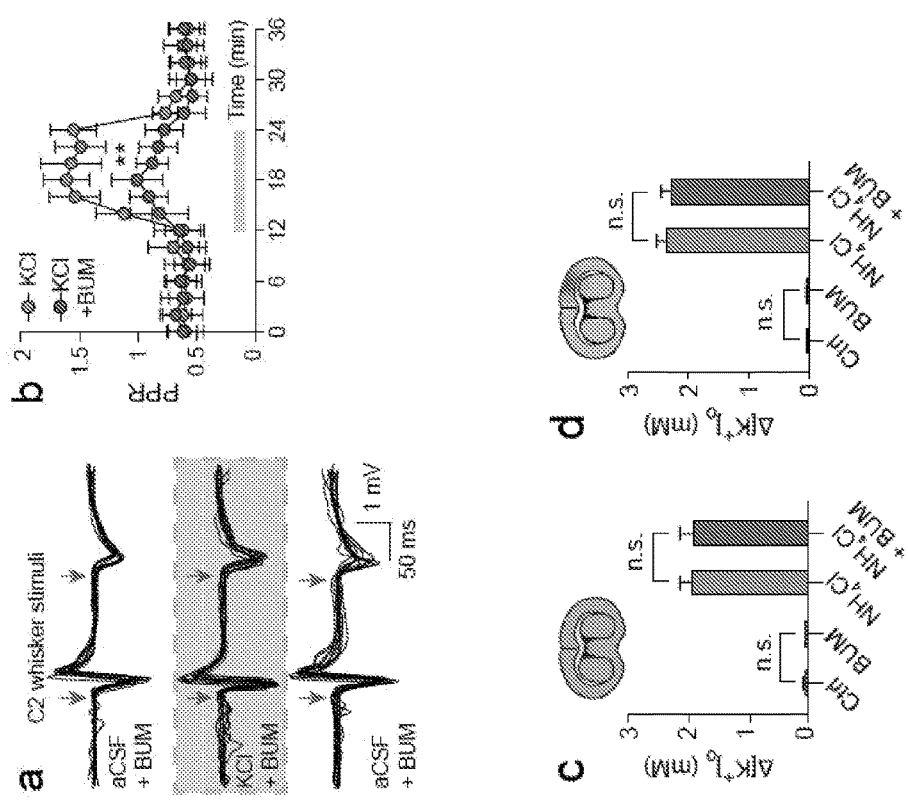
FIGS. 10A-10D illustrate that bumetanide treats potassium induced neural disinhibition.

The inhibitory action of GABA is dependent on a hyperpolarized E$_{GABA}$. Zhang et al., "Transition to Seizure: From "Macro"- to "Micro"-Mysteries," *Epilepsy Res.* 97:290-299 (2011), which is hereby incorporated by reference in its entirety. Using whole-cell voltage clamp of pyramidal neurons with ramp voltage (0 to −120 mV) and GABA application, it was found that ammonia depolarized E$_{GABA}$ by +12.33±3.66 mV (FIG. 3C). This effect was GABA$_A$-receptor dependent, as the GABA$_A$-receptor antagonist bicuculline, completely blocked the GABA-induced current (FIGS. 9A, 9B). Similar to previous studies using moderate ammonia concentrations, no consistent change was found in neuronal resting membrane potential or input resistance. Lux, H. D., "Ammonium and Chloride Extrusion: Hyperpolarizing Synaptic Inhibition in Spinal Motor Neurons," *Science* 173:555-557 (1971); Szerb et al., "Effect of Ammonium Ions on Synaptic Transmission in the Mammalian Central Nervous System," *Prog. Neurobiol.* 39:135-153 (1992), both of which are hereby incorporated by reference in their entirety.

Figures 3D, 3E, 3F, 3G, 3H:
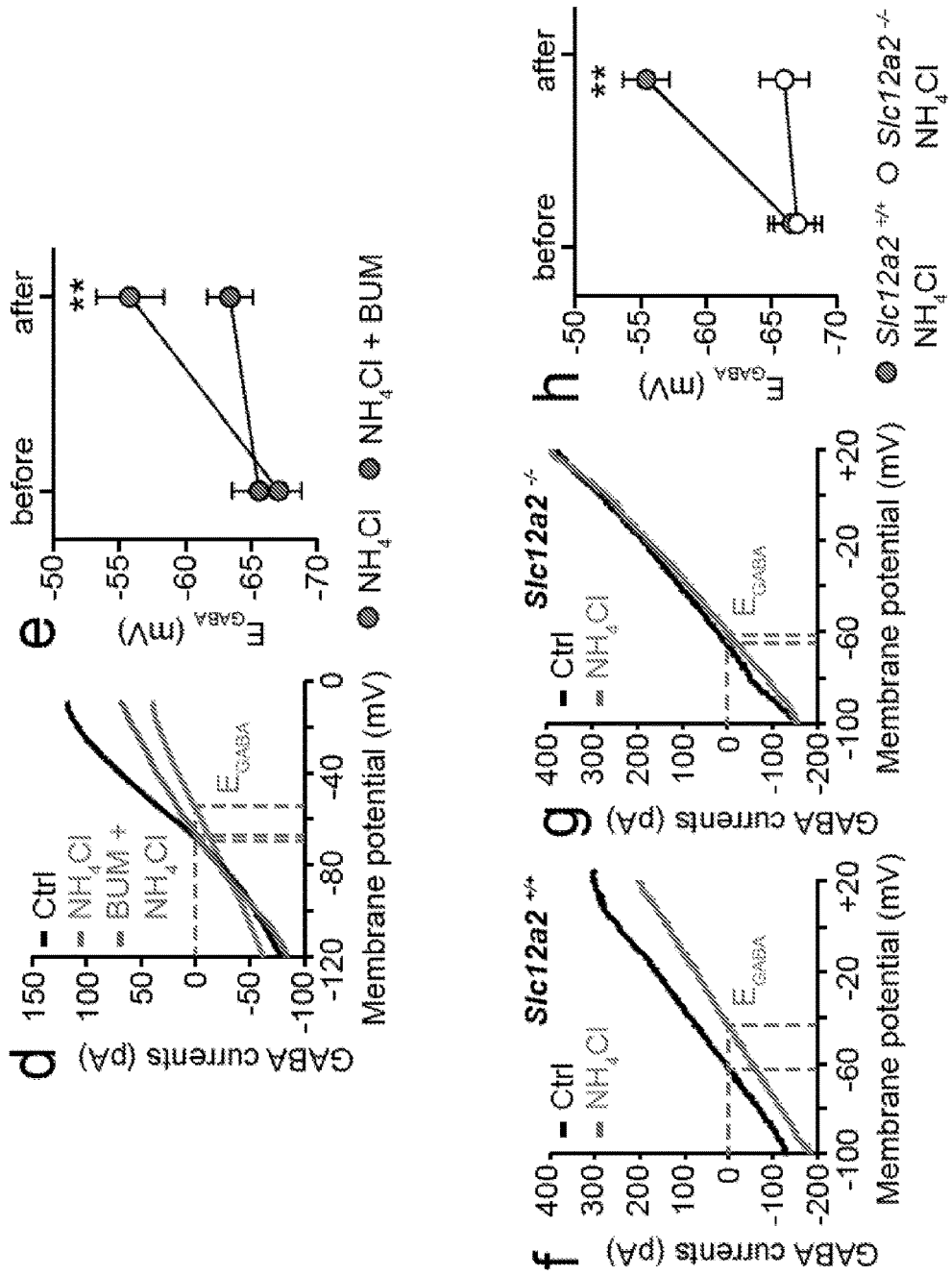

Because E$_{GABA}$ is heavily dependent on chloride transporters, the diuretic bumetanide was next tested, a highly specific NKCC1 inhibitor used in clinical practice to treat heart failure. Hannaert et al., "Rat NKCC2/NKCC1 Cotransporter Selectivity For Loop Diuretic Drugs," *Naunyn Schmiedebergs Arch. Pharmacol.* 365:193-199 (2002); Dzhala et al., "NKCC1 Transporter Facilitates Seizures in the Developing Brain," *Nat. Med.* 11:1205-1213 (2005); Koyama et al., "GABAergic Excitation After Febrile Seizures Induces Ectopic Granule Cells and Adult Epilepsy," *Nat Med* (Epub Jul. 15, 2012), which are hereby incorporated by reference in their entirety. In the present study, bumetanide (5 µM) pre-incubation successfully prevented the depolarizing effect of ammonia on $E_{GABA}$ (FIGS. 3D, 3E). To ensure the molecular specificity of bumetanide, gramicidin-perforated patch recordings were also performed in conditional NKCC1 knock-out (Slc12a2$^{-/-}$) and wild-type littermates (Slc12a2$^{+/+}$). Similar to bumetanide, NKCC1 deletion completely blocked the depolarizing effect of ammonia on $E_{GABA}$ (+11.14±1.22 in Slc12a2$^{+/+}$ and +1.00±1.07 in Slc12a2$^{-/-}$) (FIGS. 3F-3H).

Figure 3I:
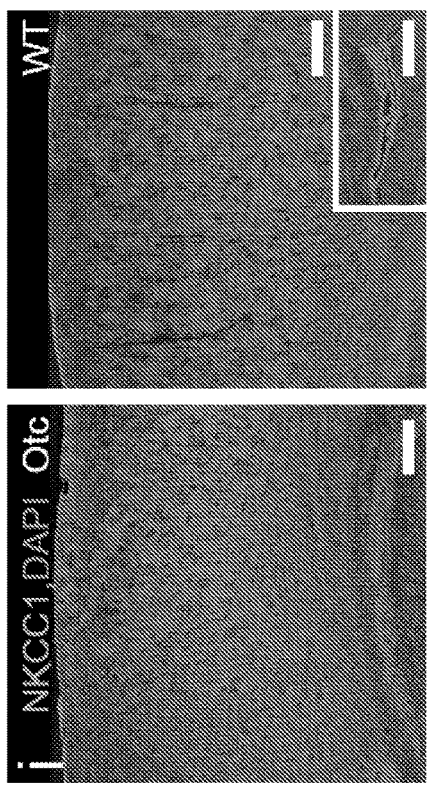

Using immunohistochemistry, it was found that NKCC1 is present in cortex (FIG. 3I), confirming previous studies indicating NKCC1 expression in adult brain, although at lower levels than in developing tissue. Dzhala et al., "NKCC1 Transporter Facilitates Seizures in the Developing Brain," *Nat. Med.* 11:1205-1213 (2005); Kanaka et al., "The Differential Expression Patterns of Messenger RNAs Encoding K—Cl Cotransporters (KCC1,2) and Na-K-2Cl Cotransporter (NKCC1) in the Rat Nervous System," *Neuroscience* 104:933-946 (2001); Chen et al., "Na(+)-Dependent Chloride Transporter (NKCC1)-Null Mice Exhibit Less Gray and White Matter Damage After Focal Cerebral Ischemia," *J. Cereb. Blood Flow Metab.* 25:54-66 (2005), all of which are hereby incorporated by reference in their entirety. No obvious differences were observed in the expression pattern of NKCC1 between wild-type and Otc$^{spf-ash}$ mice throughout the cortex. Interestingly, chronic low elevations of ammonia similar to the resting levels seen in the Otc$^{spf-ash}$ mice have been shown to increase NKCC1 activity up to three fold, perhaps explaining some of the baseline learning deficit in these mice. Jayakumar et al. "The Na—K—Cl Cotransporter in the Brain Edema of Acute Liver Failure," *J. Hepatol.* 54:272-278 (2011), which is hereby incorporated by reference in its entirety. Finally, similar to previous $^1$H-NMR studies no net change was found in the levels of neurotransmitters glutamate and GABA to explain the ammonia-induced disinhibition (Table 3, infra). Ratnakumari et al., "Na+,K(+)-ATPase Activites are Increased in Brain in Both Congenital and Acquired Hyperammonemic Syndromes," *Neurosci. Lett.* 197:89-92 (1995); Zwingmann et al., "Selective Increase of Brain Lactate Synthesis in Experimental Acute Liver Failure: Results of a [1H-13C] Nuclear Magnetic Resonance Study," *Hepatology* 37:420-428 (2003), which are hereby incorporated by reference in their entirety.

In Table 3, $^1$H-NMR was used to determine amino acid concentrations (µmol g$^{-1}$ wet weight) 30 minutes after saline (Ctrl) or ammonia administration (7.5 mmol kg$^{-1}$ i.p.). Data are shown as mean±SEM.

Figure 3J:
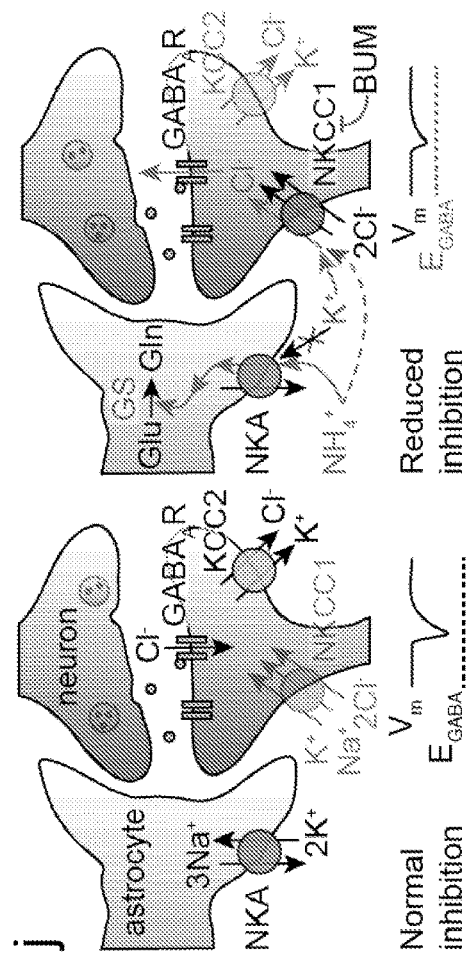

On the basis of these observations, it was hypothesized that elevated [K$^+$]$_o$ and [NH$_4^+$]$_o$ overactivate neuronal NKCC1, leading to an intracellular accumulation of chloride that depolarizes $E_{GABA}$ (FIG. 3J). Supporting this conclusion, previous in vivo, in situ and in vitro work has shown that neurons exposed to elevated ammonia levels have significantly increased intracellular chloride content. Lux, H. D., "Ammonium and Chloride Extrusion: Hyperpolarizing Syntaptic Inhibition in Spinal Motor Neurons," *Science* 173:555-557 (1971); Irie et al., "Chloride Concentration in Cultured Hippocampal Neurons Increases During Long-Term Exposure to Ammonia Through Enhanced Expression of an Anion Exchanger," *Brain Research* 806:246-256 (1998); Benjamin, A. M., "Effects of Ammonium Ions on Spontaneous Action Potentials and on Contents of Sodium, Potassium, Ammonium, and Chloride Ions in Brain In Vitro," *J. Neurochem.* 30:131-143 (1978), all of which are hereby incorporated by reference in their entirety.

Example 9—NKCC1 Inhibition Rescues Ammonia Induced Neurological Impairment

Figures 4A, 4B, 4C, 4D:
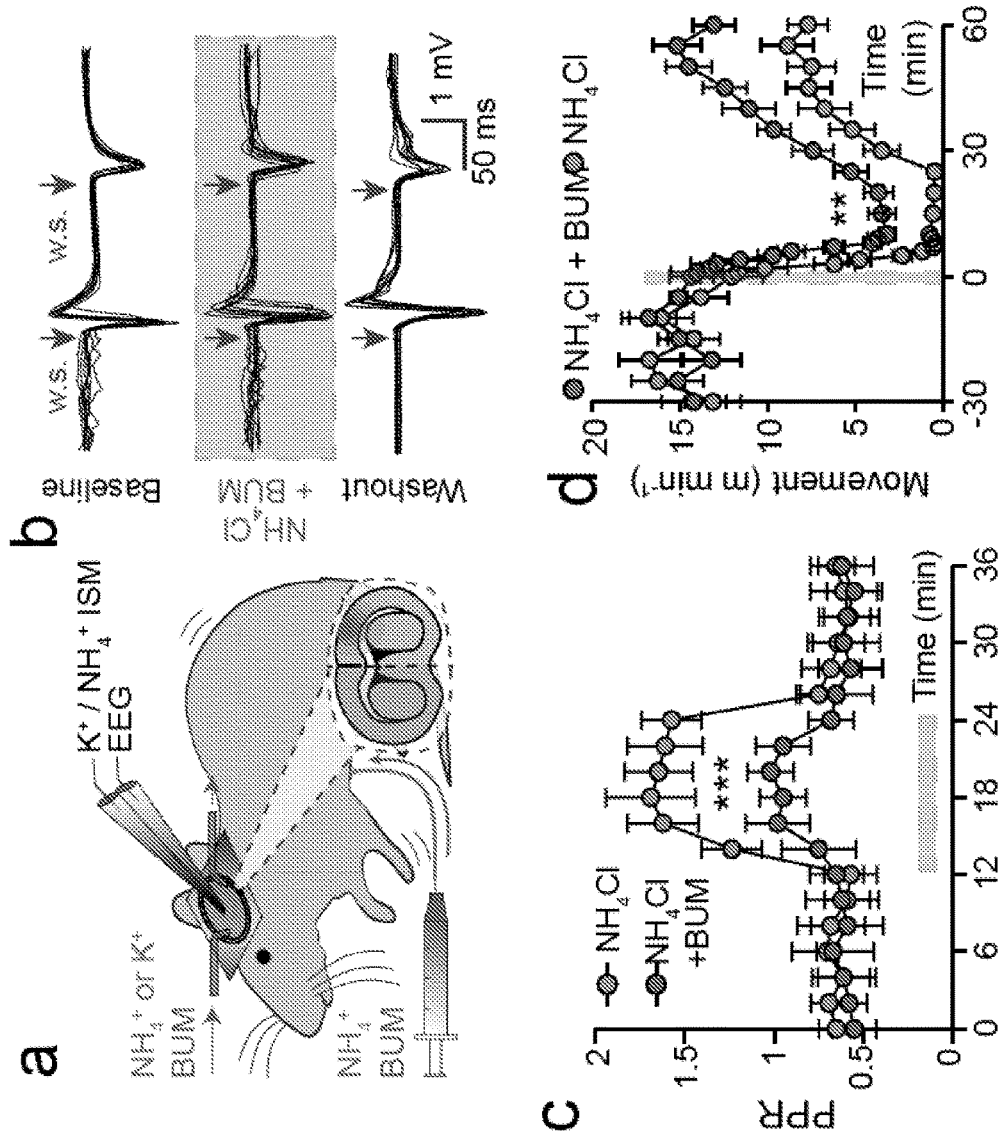
FIGS. 4A-4G show that NKCC1 inhibition with bumetanide (BUM) potently treats the electrophysiological and clinical features of ammonia neurotoxicity.
Figures 4E, 4F, 4G:
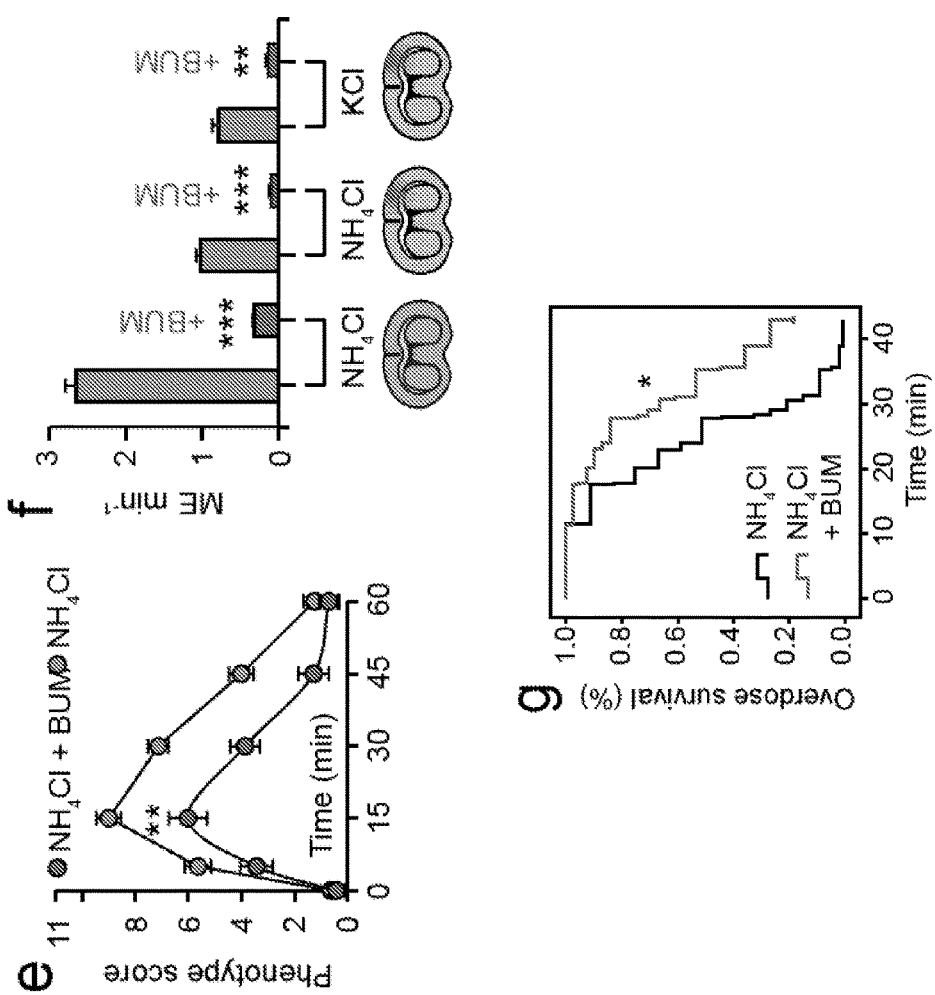

To test the validity of the present in situ model, awake animals were tested (FIG. 4A). Using the previously described paired-pulse paradigm, it was found that bumetanide significantly improved disinhibition following cortical application of both ammonia and potassium (PPR 0.88±0.15 following ammonia+bumetanide application, PPR 0.59±0.17 after washout of both, PPR 0.92±0.18 following KCl+bumetanide) (FIGS. 4B, 4C, 10A, 10B). To investigate whether this improvement of neuronal function translated into a clinically relevant improvement in disease phenotype, the phenotype measures outlined in FIGS. 1A-1I were employed. It was found that NKCC1 inhibition increased spontaneous mouse movement (0.42±0.22 to 3.17±0.46 m min$^{-1}$), reduced the sensory-motor phenotype score (9.00±0.46 to 6.00±0.72) and decreased ME frequency (0.78±0.05 to 0.13±0.03 with cortical KCl, 1.02±0.07 to 0.10±0.02 with cortical NH$_4$Cl and 2.66±0.14 to 0.32±0.02 ME min$^{-1}$ with systemic NH$_4$Cl) (FIGS. 4D-4G). Moreover, survival after ammonia overdose (10 mmol kg$^{-1}$) increased by a factor of 3.87 (hazard rate ratio 0.26, 95% confidence interval 0.08 to 0.87). These clinically relevant improvements were observed both when bumetanide was administered systemically (i.p., 30 mg kg$^{-1}$) and cortically (5 µM), indicating that the drug exerts its beneficial action principally in the cortex. Moreover, the therapeutic effect of bumetanide could not be attributed to a normalization of [K$^+$]$_o$, [NH$_4^+$]$_o$ or brain amino acids, which were unaltered

TABLE 3

Biochemical Changes During Acute Ammonia Neurotoxicity.

| | Genotype: | | | | | | |
|---|---|---|---|---|---|---|---|
| | WT | WT | WT | Otc$^{spf-ash}$ | Otc$^{spf-ash}$ | Otc$^{spf-ash}$ | Otc$^{spf-ash}$ |
| | Exposure: | | | | | | |
| | Ctrl | BUM | NH$_4$ | Ctrl | BUM | NH$_4$ | BUM NH$_4$ |
| Glutamate | 14.29 ± 0.19 | 14.38 ± 0.22 | 12.49 ± 0.15 | 14.67 ± 0.68 | 14.27 ± 0.23 | 13.24 ± 0.33 | 12.51 ± 0.37 |
| Glutamine | 4.85 ± 0.47 | 4.52 ± 0.18 | 8.69 ± 0.33 | 7.58 ± 0.52 | 8.70 ± 1.54 | 9.25 ± 0.34 | 11.44 ± 0.46 |
| GABA | 2.00 ± 0.13 | 2.55 ± 0.05 | 2.19 ± 0.12 | 2.53 ± 0.12 | 2.39 ± 0.13 | 2.46 ± 0.13 | 2.23 ± 0.08 | by the treatment (FIG. 10A-10D, Tables 1-3). These in vivo data demonstrate the importance of NKCC1 in ammonia neurotoxicity, and support the model developed from the in situ data (see FIG. 3J).

Ammonia neurotoxicity is an almost universal phenomenon that occurs in all animals from fish to humans, and has previously been extensively studied in vitro, in situ, and using biochemical or histological methods. This previous work has produced important clues as to the cellular mechanisms underlying ammonia neurotoxicity, but the continued lack of treatment clearly illustrates that the overall picture is still incomplete. The present invention tested and extended individual ex vivo observations using in vivo models, where experimental observations can be continuously correlated with clinical phenotype. In this way, a more complete picture of what cellular and subcellular changes are necessary and sufficient to produce the neurological dysfunction seen in acute ammonia neurotoxicity (e.g. elevated $[K^+]_o$), and which are not (e.g. astrocyte swelling) was pieced together. All anesthetics tested in the present invention masked the ammonia induced neurological phenotype and disrupted normal astrocyte signaling. Thus, the use of awake animals in the in vivo models was critical to identify the pathological chain of events involving both astrocytes and neurons that leads to ammonia neurotoxicity.

First, the childhood disorder of X-linked OTC deficiency was used to develop a clean mouse model of acute ammonia neurotoxicity that was unconfounded by hemodynamic or hepatic complications. Ye et al. "Adenovirus-Mediated In Vivo Gene Transfer Rapidly Protects Ornithine Transcarbamylase-Deficient Mice From an Ammonium Challenge," *Pediatr. Res.* 41:527-535 (1997), which is hereby incorporated by reference in its entirety. Using behavioral and biochemical methods it was shown that this model replicates all the pathognomic features of ammonia neurotoxicity. This relatively rare disorder thus represents an important opportunity to try and understand the toxic effects of ammonia on neural tissue.

Second, using paired-pulse whisker stimulation in awake mice, it was shown that an acute ammonia challenge causes disinhibition of neuronal firing and consequently myoclonic events similar to those observed in children with OTC deficiency. Cagnon et al., "Hyperammonemia-Induced Toxicity for the Developing Central Nervous System," *Brain Res. Rev.* 56:183-197 (2007), which is hereby incorporated by reference in its entirety. Additionally, evidence is provided suggesting that these myoclonic events originate in the cortex, likely due to the rapid influx of ammonia into cortical astrocytes driven by the enzyme glutamine synthetase. Finally, it is shown that the neurological phenotype in ammonia neurotoxicity can be reproduced using a novel model where ammonia is applied directly to cortex of awake mice.

Third, due to the putatively four times larger ammonia load on astrocyte membranes than all other cell types, it was next asked how astrocytes contribute to or cause the neuronal dysfunction. Extensive ex vivo literature suggests that ammonia causes brisk astrocyte swelling. Butterworth, R. F., "Pathophysiology of Hepatic Encephalopathy: A New Look at Ammonia," *Metab. Brain Dis.* 17:221-227 (2002); Jayakumar et al., "Glutamine in the Mechanism of Ammonia-Induced Swelling," *Neurochem. Int.* 48:623-628 (2006); Rama Rao et al., "Brain Aquaporin-4 in Experimental Acute Liver Failure," *J. Neuropath. Exper. Neurol.* 69:869-879 (2010); Zielinska et al., "Excitotoxic Mechanism of Cell Swelling in Rat Cerebral Cortical Slices Treated Acutely With Ammonia," *Neurochem. Int.* 43:299-303 (2003), all of which are hereby incorporated by reference in their entireties. Surprisingly, however, it was found that ammonia does not cause astrocyte swelling, but instead results in changes in astrocyte calcium signaling. It is suggested here that the signaling changes represent astrocytic compensatory responses to neuronal hyperexciteability, astrocyte distress, and/or dysfunction of astrocytes early in the disease process. This is the first examination of astrocyte volume and signaling changes in vivo during ammonia neurotoxicity.

Fourth, the exploration of whether dysfunctional astrocyte signaling was indicative of impaired astrocyte potassium uptake was undertaken, as the two are closely linked. Wang et al., "Astrocytes Modulate Neural Network Activity by Ca(2)(+)-Dependent Uptake of Extracellular K(+)," *Science Signaling* 5:ra26 (2012), which is incorporated by reference in its entirety. Using the awake mouse models of systemic and direct cortical ammonia neurotoxicity, it was observed that a ~2 mM $[K^+]_o$ increase preceded symptom onset. Notably, the magnitude of the $[K^+]_o$ increase correlated closely with disease severity. The neural and clinical features of ammonia neurotoxicity by cortical application of potassium alone were reproduced. This is the first direct link between potassium and neural dysfunction, including seizures, in ammonia intoxication.

Fifth, it is demonstrated that $NH_4^+$ can compete with $K^+$ ions for active uptake on astrocyte membranes. This competition short circuits the astrocytic NKA pump with severe consequences, including compromised $[K^+]_o$ buffering and seizures. A similar competition has been shown in kidney and retina, suggesting that an accumulation of ammonia may act as a universal hazard that can disrupt potassium homeostasis in any organ and almost any animal. Marcaggi et al., "Neuron-Glial Trafficking of $NH4^+$ and $K^+$: Separate Routes of Uptake Into Glial Cells of Bee Retina," *Eur. J. Neurosci.* 19:966-976 (2004); Wall et al., "NH4+Transport Mediated by Na(+)-K(+)-ATPase in Rat Inner Medullary Collecting Duct," *Am. J. Physiol.* 267:F660-670 (1994), both of which are hereby incorporated by reference in their entirety.

Finally, it is shown that there is currently no effective way (e.g. MSO) of protecting astrocytes from ammonia without increasing the ammonia load on neurons. However, it was found that inhibiting the downstream effects of ammonia and potassium on neurons is the most effective therapeutic strategy. These downstream effects appear to critically depend on a potassium-driven depolarizing shift in $E_{GABA}$ that impairs neural inhibition. It is shown that inhibiting the chloride importer NKCC1 with the clinically used diuretic bumetanide not only rescues the shift in $E_{GABA}$, but also improves all aspects of the neurological phenotype.

Myoclonic events are characterized by generalized poly-spike-and-wave discharges on the EEG. Blumenfeld, H., "Cellular and Network Mechanisms of Spike-Wave Seizures," *Epilepsia* 46:21-33 (2005), which is hereby incorporated by reference in its entirety. Poly-spike-and-wave discharges are observed in a group of seizure disorders, including childhood absence seizures, which have recently been shown to involve early cortical activation. Bai et al., "Dynamic Time Course of Typical Childhood Absence Seizures: EEG, Behavior, and Functional Magnetic Resonance Imaging," *J. Neurosci.* 30:5884-5893 (2010), which is hereby incorporated by reference in its entirety. This led to the hypothesis that poly-spike-and-wave discharges originate from a focus in the cortex, before recruiting the thalamus leading to generalized seizures. Notably, during poly-spike-and-wave discharges, injection of lidocaine into the cortex to locally inhibit neuronal firing is able to suppress all seizure activity in the brain. Sitnikova et al., "Cortical Control of Generalized Absence Seizures: Effect of Lidocaine Applied to the Somatosensory Cortex in WAG/Rij Rats," *Brain Res.* 1012:127-137 (2004), which is hereby incorporated by reference in its entirety. In the present invention, two lines of evidence suggest that the myoclonic events observed during ammonia neurotoxicity are cortical in origin. First, poly-spike-and-wave discharges in the cortex were recorded 8 ms prior to the thalamus. Second, direct application of ammonia or potassium on the cortex replicated the poly-spike-and-wave activity seen in systemic ammonia toxicity. Taken together, these data suggest that an impairment of potassium homeostasis in the cortex is sufficient to generate myoclonic events in the model of the present invention.

In the present invention, it was found that ammonia and potassium induced neurological impairment was preceded by a depolarizing shift in neuronal $E_{GABA}$. A similar shift in $E_{GABA}$ has been shown in resected hippocampi from patients with temporal lobe epilepsy. Huberfeld et al., "Perturbed Chloride Homeostasis and GABAergic Signaling in Human Temporal Lobe Epilepsy," *J. Neurosci.* 27:9866-9873 (2007), which is hereby incorporated by reference in its entirety. Interestingly, administration of the astrocyte toxin fluoroacetate or insulin-induced hypoglycemia also depolarized $E_{GABA}$. Raabe, W. A., "Ammonia and Disinhibition in Cat Motor Cortex by Ammonium Acetate, Monofluoroacetate and Insulin-Induced Hypoglycemia," *Brain. Res.* 210: 311-322 (1981), which is hereby incorporated by reference in its entirety. In adults, the inhibitory action of GABA is dependent on a hyperpolarized $E_{GABA}$. In early development, however, cortical neurons have a depolarized $E_{GABA}$ due to the high activity of NKCC1, which causes an intracellular accumulation of chloride. Yamada et al., "Cl– Uptake Promoting Depolarizing GABA Actions in Immature Rat Neocortical Neurones is Mediated by NKCC1," *J. Physiol.* 557:829-841 (2004), which is hereby incorporated by reference in its entirety. Early studies using radiolabelled $^{36}Cl^-$ and intracellular electrodes found a similar chloride accumulation during acute ammonia exposure, although the mechanism was not known. Lux, H. D., "Ammonium and Chloride Extrusion: Hyperpolarizing Syntaptic Inhibition in Spinal Motor Neurons," *Science* 173:555-557 (1971); Benjamin, A. M., "Effects of Ammonium Ions on Spontaneous Action Potentials and on Contents of Sodium, Potassium, Ammonium, and Chloride Ions in Brain In Vitro," *J. Neurochem.* 30:131-143 (1978), both of which are hereby incorporated by reference in their entirety. Later in development, decreased activity of NKCC1 and increased activity of K cotransporter isoform 2 (KCC2), cause a developmental switch in $E_{GABA}$ making it hyperpolarized. Blaesse et al., "Cation-Chloride Cotransporters and Neuronal Function," *Neuron* 61:820-838 (2009), which is hereby incorporated by reference in its entirety. Inhibition of NKCC1 has therefore been suggested as a therapy for seizures in early development (neonates). Dzhala et al., "NKCC1 Transporter Facilitates Seizures in the Developing Brain," *Nat. Med.* 11:1205-1213 (2005), which is hereby incorporated by reference in its entirety. Moreover, KCC2 expression is reduced following nerve injury in adults, depolarizing $E_{GABA}$, causing inappropriate neuronal firing and neuropathic pain. Coull et al., "BDNF From Microglia Causes the Shift in Neuronal Anion Gradient Underlying Neuropathic Pain," *Nature* 438: 1017-1021 (2005), which is hereby incorporated by reference in its entirety. In the model of the present invention, increased $[NH_4^+]_o$ and $[K^+]_o$ drive an NKCC1-dependent depolarizing shift in $E_{GABA}$, resembling early development. Using awake behaving adult mice, the present invention demonstrates that this depolarizing shift is followed by a severe impairment of cortical inhibitory neurotransmission and seizures.

The FDA-approved diuretic bumetanide considerably improved clinically relevant behavioral measures in the awake models of ammonia and potassium induced neurotoxicity. During childhood an accumulation of ammonia is most frequently caused by enzyme deficiencies such as the Otc mutation explored in the present invention. These devastating conditions have attracted limited research focus, and consequently the disease mechanisms are incompletely understood. Butterworth, R. F., "Pathophysiology of Hepatic Encephalopathy: A New Look at Ammonia," *Metab. Brain Dis.* 17:221-227 (2002); Lichter-Konecki et al., "Gene Expression Profiling of Astrocytes From Hyperammonemic Mice Reveals Altered Pathways for Water and Potassium Homeostasis In Vivo," *Glia* 56:365-377 (2008), both of which are hereby incorporated by reference in their entirety. Few mechanism-specific therapies have been developed for acute ammonia neurotoxicity, and bumetanide may bridge the gap in ammonia-related translational research, providing a safe, effective and mechanism-targeted therapeutic option. The present invention provides a clear impetus for the initiation of clinical trials investigating the therapeutic potential of bumetanide in ammonia neurotoxicity.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating epileptic seizures in a subject comprising:
   selecting a subject susceptible to epileptic seizures and having ammonia neurotoxicity in astrocytes, and
   administering a $Na^+$-$K^+$-$2Cl^-$ cotransporter isoform 1 ("NKCC1") inhibitor to the selected subject under conditions effective to treat epileptic seizures.

2. The method of claim 1, wherein the NKCC1 inhibitor is selected from the group consisting of bumetanide, furosemide, piretanide, azosemide, ethacrynic acid, torsemide, muzolimine, tripamide, and etozolin.

3. The method of claim 1 further comprising:
   repeating said administering.

4. The method of claim 1, wherein said administering is carried out orally, by inhalation, by intranasal instillation, topically, transdermally, parenterally, subcutaneously, intravenous injection, intra-arterial injection, intramuscular injection, intraplurally, intraperitoneally, or by application by mucous membrane.

5. A method of inhibiting accumulation of potassium surrounding astrocytes comprising:
   selecting a subject exhibiting accumulation of potassium surrounding astrocytes, and
   administering to the selected subject a $Na^+$-$K^+$-$2Cl^-$ cotransporter isoform 1 ("NKCC1") inhibitor under conditions effective to inhibit accumulation of potassium surrounding the astrocytes.

6. The method of claim 5, wherein the NKCC1 inhibitor is selected from the group consisting of bumetanide, furosemide, piretanide, azosemide, ethacrynic acid, torsemide, muzolimine, tripamide, and etozolin.

7. The method of claim 1 further comprising administering a second agent.

* * * * *